(12) United States Patent
Knodel et al.

(10) Patent No.: US 9,566,048 B1
(45) Date of Patent: Feb. 14, 2017

(54) SURGICAL INSTRUMENT WITH DISCRETE CAMMED ARTICULATION

(75) Inventors: Bryan D. Knodel, Flagstaff, AZ (US); Jinhoon Park, Mountain View, CA (US); Radulf B. R. Bosuego, Newark, CA (US)

(73) Assignee: Cardica, Inc., Redwood City ( * ) Notice: Subject to any disclaimer, the term of this patent is extended or adjusted under 35 U.S.C. 154(b) by 685 days.

(21) Appl. No.: 13/439,639

(22) Filed: Apr. 4, 2012

Related U.S. Application Data

(63) Continuation-in-part of application No. 13/094,716, filed on Apr. 26, 2011.

(51) Int. Cl.
| | | |
|---|---|---|
| *A61B 17/00* | (2006.01) | |
| *A61B 17/04* | (2006.01) | |
| *A61B 17/068* | (2006.01) | |
| *A61B 17/072* | (2006.01) | |
| *A61B 17/29* | (2006.01) | |

(52) U.S. Cl.
CPC .......... *A61B 17/00* (2013.01); *A61B 17/07207* (2013.01); *A61B 2017/00473* (2013.01); *A61B 2017/2923* (2013.01); *A61B 2017/2927* (2013.01)

(58) Field of Classification Search
CPC ................. A61B 17/07207; A61B 2017/2927; A61B 2017/00473; A61B 2017/2923
USPC ........................................... 227/175.1–182.1
See application file for complete search history.

(56) References Cited

U.S. PATENT DOCUMENTS

| | | |
|---|---|---|
| 2,515,366 A | 7/1950 | Zublin |
| 3,191,455 A | 6/1965 | Fuqua et al. |
| D210,021 S | 1/1968 | Prifogle |
| 3,497,608 A | 2/1970 | Elliott |
| 3,581,551 A | 6/1971 | Wilkinson |
| 3,583,393 A | 6/1971 | Takahashi |
| 3,650,453 A | 3/1972 | Smith, Jr. |
| 3,837,555 A | 9/1974 | Green |
| 3,899,914 A | 8/1975 | Akiyama |
| 3,986,765 A | 10/1976 | Shaffer |
| 4,086,926 A | 5/1978 | Green et al. |

(Continued)

FOREIGN PATENT DOCUMENTS

| | | |
|---|---|---|
| EP | 1238634 | 9/1994 |
| EP | 2258281 | 12/2010 |

(Continued)

OTHER PUBLICATIONS

Notification of Transmittal of the International Search Report and the Written Opinion of the International Searching Authority, PCT/US2013/034322, mailed Jul. 12, 2013.

(Continued)

*Primary Examiner* — Gloria R Weeks
*Assistant Examiner* — Eyamindae Jallow
(74) *Attorney, Agent, or Firm* — Vista IP Law Group, LLP

(57) ABSTRACT

One example of a surgical apparatus may include an end effector; a shaft extending proximally from the end effector, the shaft including an articulation region; a handle including at least one button; an articulation gear held by the handle, where at least one cam path is defined in the articulation gear; and at least one holder post extending into each cam path; where actuation of one button causes the end effector to articulate through a discrete angular increment relative to the shaft.

15 Claims, 24 Drawing Sheets

(56) References Cited

U.S. PATENT DOCUMENTS

| | | | |
|---|---|---|---|
| 4,127,227 A | 11/1978 | Green | |
| 4,228,895 A | 10/1980 | Larkin | |
| 4,328,839 A | 5/1982 | Lyons et al. | |
| 4,475,679 A | 10/1984 | Fleury, Jr. | |
| 4,589,416 A | 5/1986 | Green | |
| 4,600,037 A | 7/1986 | Hatten | |
| 4,633,861 A | 1/1987 | Chow et al. | |
| 4,762,260 A | 8/1988 | Richards et al. | |
| 4,869,414 A | 9/1989 | Green et al. | |
| 4,969,591 A | 11/1990 | Richards et al. | |
| 5,042,707 A | 8/1991 | Taheri | |
| 5,143,475 A | 9/1992 | Chikama | |
| 5,156,315 A | 10/1992 | Green et al. | |
| 5,192,288 A | 3/1993 | Thompson et al. | |
| 5,271,543 A | 12/1993 | Grant et al. | |
| 5,340,330 A | 8/1994 | Dolson et al. | |
| 5,381,943 A | 1/1995 | Allen et al. | |
| 5,405,073 A | 4/1995 | Porter | |
| 5,413,272 A | 5/1995 | Green et al. | |
| 5,448,989 A | 9/1995 | Heckele | |
| 5,456,400 A | 10/1995 | Shichman et al. | |
| 5,465,894 A | 11/1995 | Clark et al. | |
| 5,476,206 A | 12/1995 | Green | |
| 5,485,952 A | 1/1996 | Fontayne | |
| 5,580,067 A | 12/1996 | Hamblin et al. | |
| 5,632,432 A * | 5/1997 | Schulze et al. | 227/176.1 |
| 5,655,698 A | 8/1997 | Yoon | |
| 5,662,260 A | 9/1997 | Yoon | |
| 5,673,840 A | 10/1997 | Schulze et al. | |
| 5,692,668 A | 12/1997 | Schulze et al. | |
| 5,704,534 A * | 1/1998 | Huitema et al. | 227/175.1 |
| 5,749,828 A | 5/1998 | Solomon et al. | |
| 5,772,578 A | 6/1998 | Heimberger et al. | |
| 5,807,241 A | 9/1998 | Heimberger | |
| 5,810,855 A | 9/1998 | Rayburn et al. | |
| 5,816,471 A | 10/1998 | Plyley et al. | |
| 5,823,066 A | 10/1998 | Huitema et al. | |
| 5,855,311 A | 1/1999 | Hamblin et al. | |
| 5,857,964 A | 1/1999 | Konstorum et al. | |
| 5,894,979 A | 4/1999 | Powell | |
| 5,918,791 A | 7/1999 | Sorrentino et al. | |
| 5,964,774 A | 10/1999 | McKean et al. | |
| 6,010,054 A * | 1/2000 | Johnson et al. | 227/176.1 |
| 6,053,922 A | 4/2000 | Krause et al. | |
| 6,306,149 B1 | 10/2001 | Meade | |
| 6,364,828 B1 | 4/2002 | Yeung et al. | |
| 6,391,038 B2 | 5/2002 | Vargas et al. | |
| 6,431,904 B1 | 8/2002 | Berelsman | |
| 6,602,252 B2 | 8/2003 | Mollenauer | |
| 6,656,195 B2 | 12/2003 | Peters et al. | |
| 6,716,221 B2 | 4/2004 | Koefer et al. | |
| 6,716,232 B1 | 4/2004 | Vidal et al. | |
| 6,755,338 B2 | 6/2004 | Hahnen et al. | |
| 6,786,382 B1 | 9/2004 | Hoffman | |
| 6,817,508 B1 | 11/2004 | Racenet | |
| 6,827,601 B1 | 12/2004 | Haeberle | |
| 6,835,199 B2 | 12/2004 | McGuckin et al. | |
| 6,843,403 B2 | 1/2005 | Whitman | |
| 7,025,747 B2 | 4/2006 | Smith | |
| 7,059,508 B2 | 6/2006 | Shelton, IV et al. | |
| 7,097,089 B2 | 8/2006 | Marczyk | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,300,297 B1 | 11/2007 | Wang | |
| 7,316,575 B2 | 1/2008 | Muschketat | |
| 7,407,077 B2 | 8/2008 | Ortiz et al. | |
| 7,434,716 B2 | 10/2008 | Viola | |
| 7,481,824 B2 | 1/2009 | Gillum et al. | |
| 7,486,994 B2 | 2/2009 | Zarembo et al. | |
| 7,506,790 B2 | 3/2009 | Shelton, IV | |
| 7,507,109 B2 | 3/2009 | Tran | |
| 7,559,449 B2 * | 7/2009 | Viola | 227/175.1 |
| 7,575,144 B2 | 8/2009 | Ortiz et al. | |
| 7,585,307 B2 | 9/2009 | Fontayne et al. | |
| 7,617,961 B2 | 11/2009 | Viola | |
| 7,654,838 B1 | 2/2010 | Zhuge | |
| 7,670,334 B2 | 3/2010 | Hueil et al. | |
| 7,708,182 B2 | 5/2010 | Viola | |
| 7,810,690 B2 | 10/2010 | Bilotti | |
| 7,819,298 B2 | 10/2010 | Hall et al. | |
| 8,083,765 B2 | 12/2011 | Lee et al. | |
| 8,292,889 B2 | 10/2012 | Cunningham et al. | |
| 8,322,455 B2 | 12/2012 | Shelton, IV et al. | |
| 8,475,453 B2 | 7/2013 | Marczyk et al. | |
| 8,672,951 B2 * | 3/2014 | Smith et al. | 606/139 |
| 8,870,867 B2 | 10/2014 | Walberg et al. | |
| 2003/0120284 A1 | 6/2003 | Palacios et al. | |
| 2003/0236551 A1 | 12/2003 | Peterson | |
| 2005/0139629 A1 * | 6/2005 | Schwemberger et al. | 227/19 |
| 2005/0184121 A1 | 8/2005 | Heinrich | |
| 2005/0209685 A1 | 9/2005 | Shifrin et al. | |
| 2005/0272978 A1 | 12/2005 | Brunnen et al. | |
| 2005/0283191 A1 * | 12/2005 | Fontayne et al. | 606/219 |
| 2006/0000867 A1 * | 1/2006 | Shelton et al. | 227/175.1 |
| 2006/0011699 A1 | 1/2006 | Olson et al. | |
| 2006/0016853 A1 * | 1/2006 | Racenet | 227/176.1 |
| 2006/0025811 A1 | 2/2006 | Shelton, IV | |
| 2006/0041273 A1 | 2/2006 | Ortiz et al. | |
| 2006/0047307 A1 | 3/2006 | Ortiz et al. | |
| 2006/0151567 A1 | 7/2006 | Roy | |
| 2007/0023477 A1 * | 2/2007 | Whitman et al. | 227/175.1 |
| 2007/0027472 A1 | 2/2007 | Hiles et al. | |
| 2007/0034668 A1 | 2/2007 | Holsten et al. | |
| 2007/0068990 A1 * | 3/2007 | Shelton et al. | 227/175.1 |
| 2007/0073341 A1 | 3/2007 | Smith et al. | |
| 2007/0083234 A1 | 4/2007 | Shelton, IV et al. | |
| 2007/0118163 A1 | 5/2007 | Boudreaux et al. | |
| 2007/0125828 A1 | 6/2007 | Rethy et al. | |
| 2007/0175947 A1 | 8/2007 | Ortiz et al. | |
| 2007/0221700 A1 | 9/2007 | Ortiz et al. | |
| 2007/0221701 A1 | 9/2007 | Ortiz et al. | |
| 2008/0249364 A1 | 10/2008 | Korner | |
| 2008/0257935 A1 | 10/2008 | Viola | |
| 2008/0296345 A1 * | 12/2008 | Shelton et al. | 227/176.1 |
| 2009/0057370 A1 * | 3/2009 | Marczyk et al. | 227/179.1 |
| 2009/0065552 A1 | 3/2009 | Knodel et al. | |
| 2009/0076506 A1 | 3/2009 | Baker | |
| 2009/0090763 A1 | 4/2009 | Zemlok et al. | |
| 2009/0090764 A1 | 4/2009 | Viola | |
| 2009/0114699 A1 * | 5/2009 | Viola | 227/175.1 |
| 2009/0177041 A1 | 7/2009 | Stefanchik et al. | |
| 2009/0206123 A1 * | 8/2009 | Doll et al. | 227/175.1 |
| 2009/0206124 A1 * | 8/2009 | Hall et al. | 227/175.1 |
| 2009/0206128 A1 * | 8/2009 | Hueil et al. | 227/175.2 |
| 2009/0206129 A1 * | 8/2009 | Doll et al. | 227/175.2 |
| 2009/0206133 A1 * | 8/2009 | Morgan et al. | 227/176.1 |
| 2009/0206138 A1 * | 8/2009 | Smith et al. | 227/176.1 |
| 2009/0206139 A1 * | 8/2009 | Hall et al. | 227/176.1 |
| 2009/0206140 A1 * | 8/2009 | Scheib et al. | 227/176.1 |
| 2010/0243706 A1 * | 9/2010 | Cohen et al. | 227/176.1 |
| 2010/0308099 A1 * | 12/2010 | Marczyk et al. | 227/175.1 |
| 2011/0288573 A1 * | 11/2011 | Yates et al. | 606/170 |
| 2012/0074210 A1 * | 3/2012 | Baxter et al. | 227/180.1 |
| 2012/0080491 A1 * | 4/2012 | Shelton et al. | 227/176.1 |
| 2012/0168484 A1 * | 7/2012 | Scirica et al. | 227/175.1 |
| 2013/0112729 A1 * | 5/2013 | Beardsley et al. | 227/175.1 |
| 2014/0117066 A1 * | 5/2014 | Aranyi et al. | 227/176.1 |

FOREIGN PATENT DOCUMENTS

| | | |
|---|---|---|
| JP | 2005160933 | 6/2005 |
| RU | 2080833 | 6/1997 |
| WO | WO-81/01953 | 7/1981 |
| WO | WO-85/01427 | 4/1985 |
| WO | WO2004/103430 | 12/2004 |

(56) References Cited

FOREIGN PATENT DOCUMENTS

OTHER PUBLICATIONS

Gong, Shao W., "Perfectly flexible mechanism and integrated mechanism system design", *Mechanism and Machine Theory 39* (2004), (Nov. 2004),1155-1174.
Lim, Jonas J., et al., "A review of mechanism used in laparascopic surgical instruments", *Mechanism and Machine Theory 38*, (2003),1133-1147.
Lim, Jyue B., "Type Synthesis of a Complex Surgical Device", *Masters Thesis*, (Feb. 21, 2001).
Lim, Jonas J., et al., "Application of Type Synthesis Theory to the Redesign of a Complex Surgical Instrument", *Journal of Biomechanical Engineering* (124), (Jun. 2004),265-272.
Kolios, Efrossini et al., "Microlaparoscopy", *J. Endourology* 18(9), (Nov. 2004),811-817.
Steichen, Felicien M., et al., "Mechanical Sutures in Surgery", *Brit. J. Surg.* 60(3), (Mar. 1973),191-197.
"Cardica Microcutter Implant Delivery Device 510(k), Cover Sheet, Table 10.1,"Substantial Equivalence Comparison," and Section 12, "Substantial Equivalence Discussion"", (Oct. 18, 2010).

\* cited by examiner

SURGICAL INSTRUMENT WITH DISCRETE CAMMED ARTICULATION

This application is a continuation-in-part of U.S. patent application Ser. No. 13/094,716, filed on Apr. 26, 2011, which is hereby incorporated by reference in its entirety.

FIELD OF THE INVENTION

The invention generally relates to surgical instruments, and more specifically to the articulation of surgical instruments.

BACKGROUND

Minimally invasive surgery is performed through small incisions in the body, into which trocar ports may or may not be placed. One or more surgical instruments are inserted through each incision in order to perform the surgical procedure. In order to effectuate one of the objectives of minimally invasive surgery, which is the minimization of incisions to the body to reduce healing time and scarring, it is desirable to minimize the number of incisions made in the body. The number of incisions and their placement are determined by the particular surgical procedure to be performed and the configuration of the instruments used to carry out that procedure.

One problem encountering during the performance of a minimally invasive surgical procedure is access to the tissue to be treated. Depending on the specific anatomy of the patient, it may be difficult to reach an area to be treated with a specific surgical instrument. As a result, one or more additional incisions may need to be made in the patient in order to access that tissue. The surgeon may need to obtain a different surgical instrument, adding to the time and expense of the procedure. Additionally, where more incisions may be made or additional instruments may be utilized, it can be difficult and/or time-consuming for the surgeon to find the surgical site again.

BRIEF DESCRIPTION OF THE DRAWINGS

The use of the same reference symbols in different figures indicates similar or identical items.

DETAILED DESCRIPTION

U.S. Patent Application Publication No. 2009/0065552, published on Mar. 12, 2009 (the "Endocutter Document"), is hereby incorporated by reference herein in its entirety.

Figure 1:
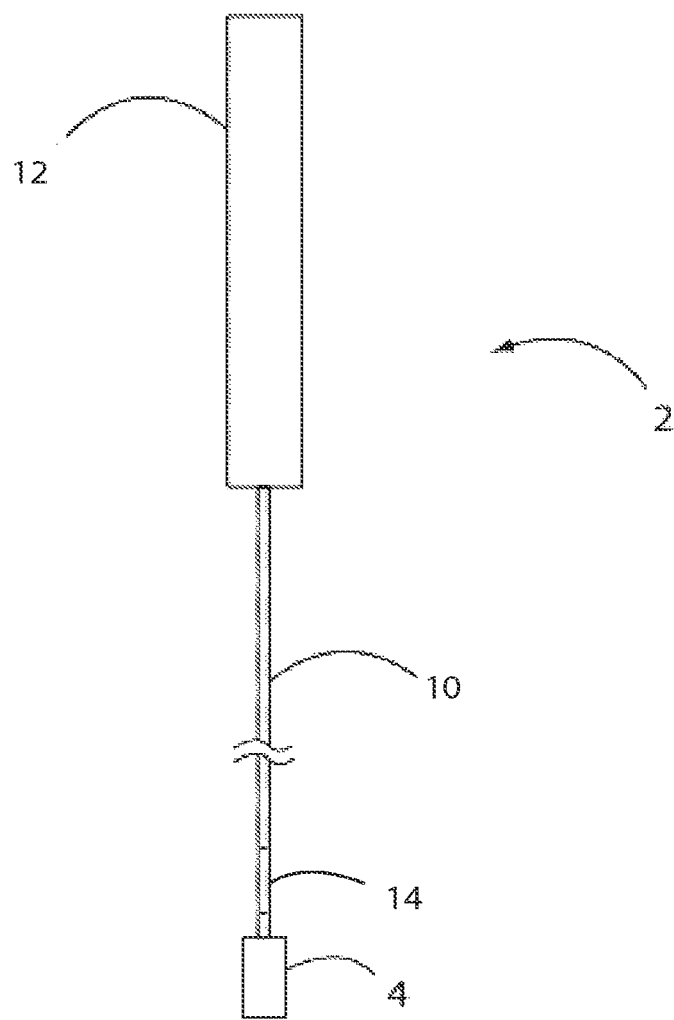
FIG. 1 is a schematic view of a surgical tool.
Figure 2:
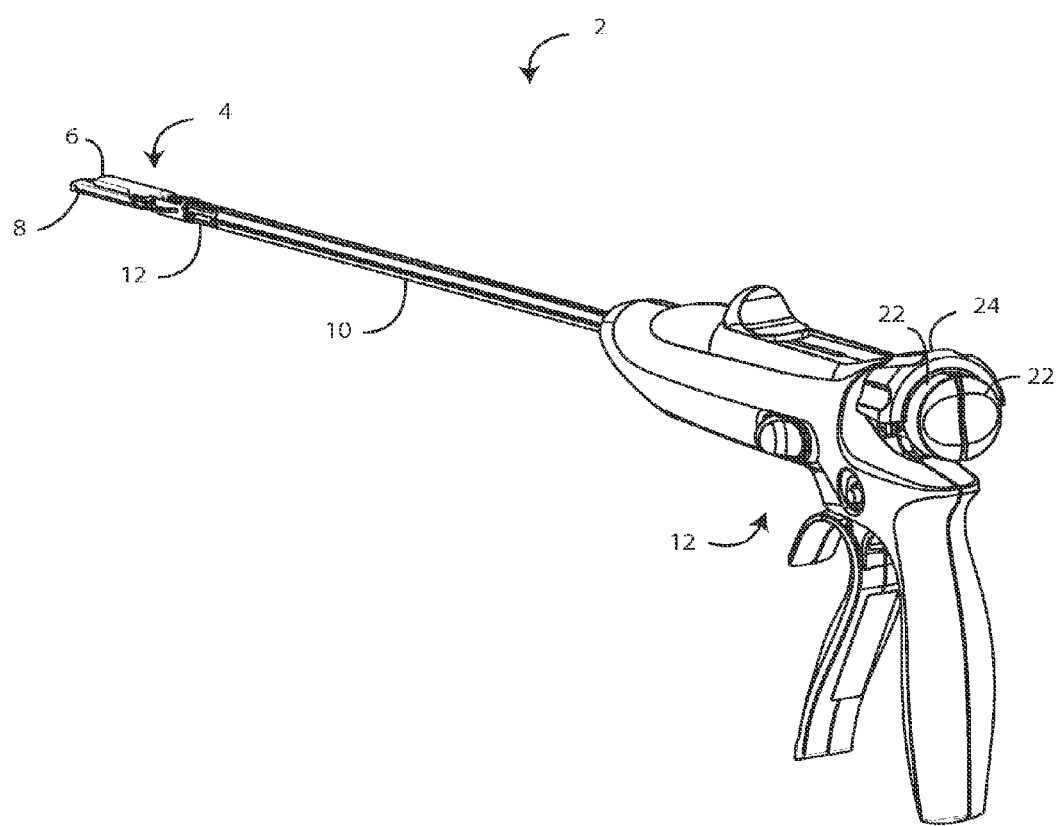
FIG. 2 is a perspective view of an exemplary surgical tool.

Referring to FIGS. 1-2, an exemplary end effector 4 of a surgical tool 2 may include a staple holder 8 and an anvil 6, where at least one of the staple holder 8 and the anvil 6 are rotatable and/or otherwise movable relative to one another. The staple holder 8 and anvil 6 need not be directly connected together in order to move relative to one another, as set forth in greater detail below. However, the staple holder 8 and the anvil 6 may be directly connected to one another in any suitable manner, if desired. The staple holder 8 and anvil 6 may be configured substantially as set forth in the Endocutter Document, as modified by the contents of this document. The staple holder 8 and anvil 6 may be fabricated from any suitable material or materials. As one example, both the staple holder 8 and anvil 6 may be fabricated from stainless steel. As another example, at least one of the staple holder 8 and anvil 6 may be fabricated at least in part from a ceramic material, to provide enhanced stiffness. As another example, the end effector 4 may be any other suitable item for treating or visualizing tissue, such as but not limited to at least one electrode (bipolar or otherwise), adhesive applicator, camera, ultrasound emitter, forceps, or other items. The end effector 4 may be connected to the distal end of a shaft 10. The shaft 10 may be rigid along part or all of its length, and/or may include an articulating region 12, such as described in U.S. patent application Ser. No. 12/400,760, filed on Mar. 9, 2009 (the "Articulation Document"), which is hereby incorporated by reference in its entirety. As another example, the shaft 10 may be proximally spaced apart from the end effector 4, such that the articulating region 14 is connected to the end effector 4 and thereby spaces the shaft 10 apart from the end effector 4.

The handle 12 may be attached to the proximal end of the shaft 10, or any other suitable portion of the shaft 10. The shaft 10 may be fabricated integrally with the handle 12. Alternately, the shaft 10 and the handle 12 may be two separate items that are connected together in any suitable manner. The handle 12 may include any mechanism, mechanisms, structure or structures that are suitably configured to actuate the end effector 4. The handle 12 may be actuated purely by hand, meaning that the handle 12 mechanically converts force applied thereto by hand to force utilized to actuate the end effector 4. As another example, the handle 12 may include a source of stored energy for actuating the end effector 4. The source of stored energy may be mechanical (such as a spring), electrical (such as a battery), pneumatic (such as a cylinder of pressurized gas) or any other suitable source of stored energy. The source of stored energy, its regulation, and its use in actuating the end effector 4 may be as described in the U.S. patent application Ser. No. 11/054,265, filed on Feb. 9, 2005, which is herein incorporated by reference in its entirety. The handle 12 may instead, or also, include a connector or connectors suitable for receiving stored energy from an external source, such as a hose connected to a hospital utility source of pressurized gas or of vacuum, or an electrical cord connectable to a power source.

Figure 3:
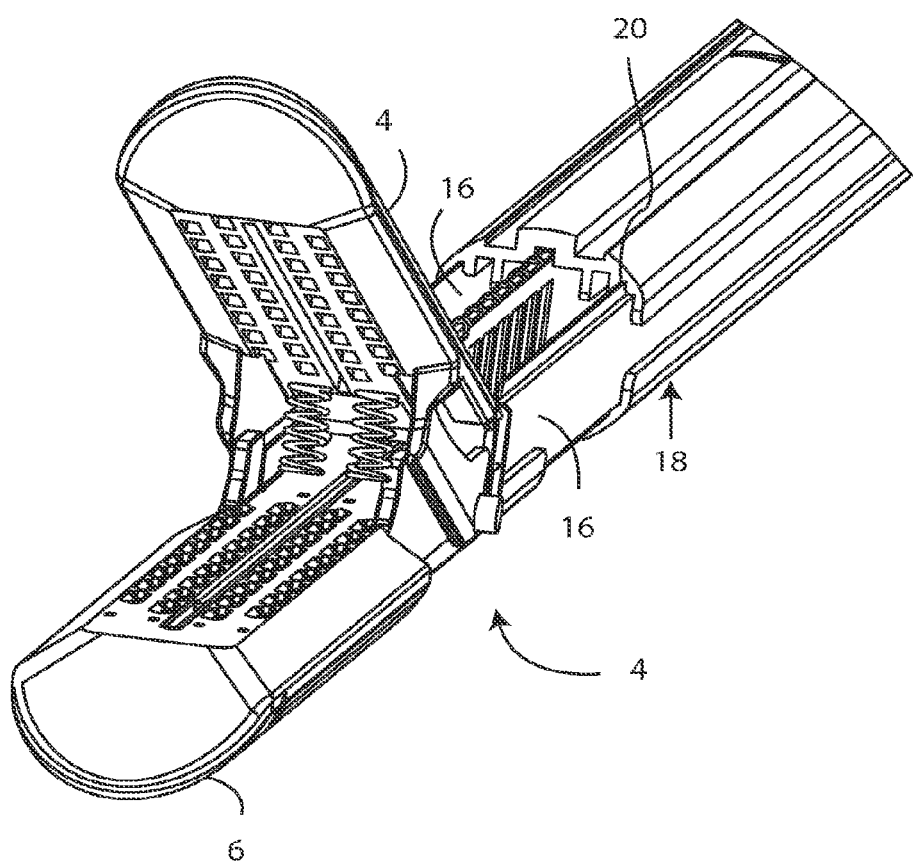
FIG. 3 is a perspective view of the end effector of the exemplary surgical tool of FIG. 2.
Figure 4:
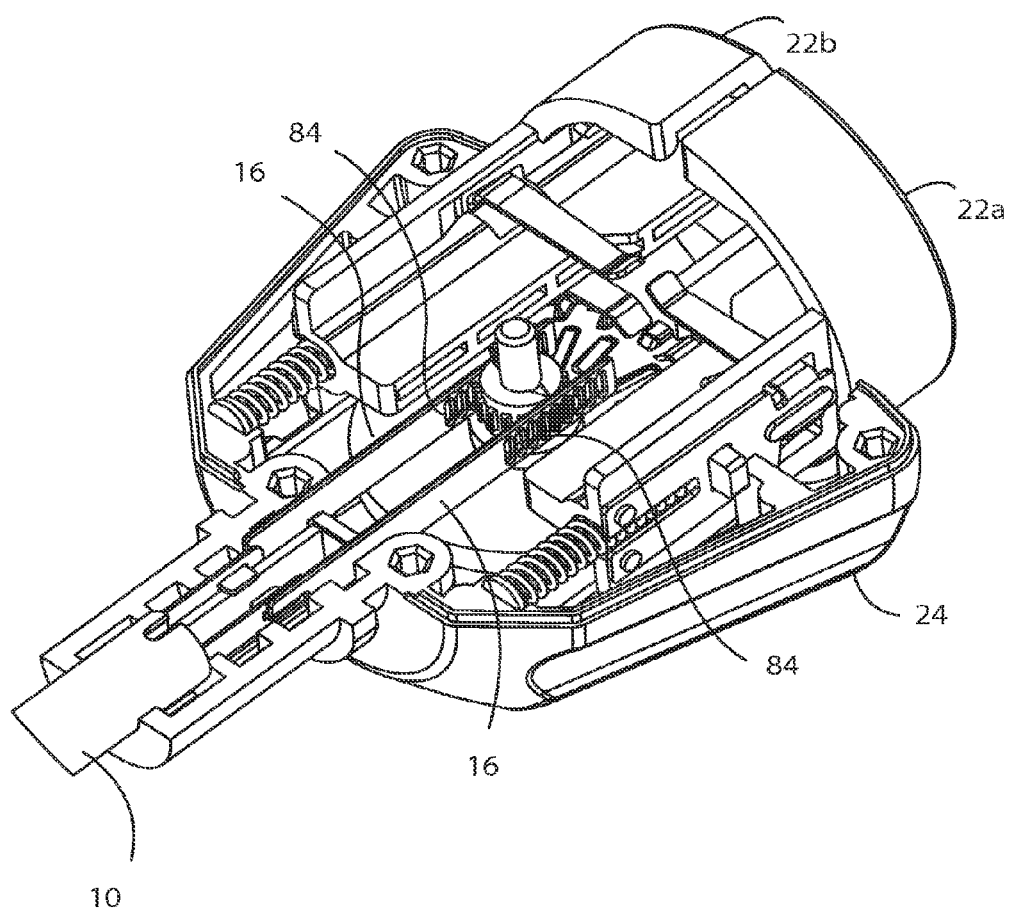
FIG. 4 is a perspective cutaway view of an articulation assembly located in the handle of the exemplary surgical tool of FIG. 2, in a neutral configuration.

Referring to FIGS. 3-4, one or more articulation bands 16 extend proximally from the end effector 4 through the articulation region 14 and the shaft 10 to the handle 12. The articulation bands 16 may be generally rectangular in cross section, where the bands 16 may be significantly greater in the height dimension than in the lateral dimension. In this way, the articulation bands 16 have a suitably low moment of inertia to allow lateral flexing of the articulation region 14. Alternately, the articulation bands 16 may have any other suitable cross-section, and such cross-section need not be constant along the length of either articulation band 16. Further, the articulation bands 16 may be composed of a material such as spring steel that allows the articulation bands 16 to provide resistance to compressive force. Each articulation band 16 may be fixed at or near its distal end to the end effector 4 by welding, adhesive, or any other suitable connection. Each articulation band 16 may extend to a different lateral side of the end effector 4. Alternately, at least one articulation band 16 may be oriented relative to the end effector 4.

A central core 18 may be located proximal to the end effector 4. The central core 18 may be fixed to the end effector 4, such as at or near the proximal end of the end effector 4. As another example, the central core 18 may be compressed between the end effector 4 and the shaft 6 or a fitting in the shaft 6 proximal to the articulation region 14. The central core 18 may extend into and/or completely through the articulation region 14. Consequently, at least the portion of the central core 18 that is located in the articulation region 14 is flexible and/or bendable. As one example, at least the portion of the central core 18 located in the articulation region 14 may be composed of a flexible material, such as but not limited to silicone or elastomer. This flexible material may be resilient, meaning that it tends to return to a neutral state after deflection, or nonresilient, meaning that it tends to remain in a deflected state after deflection. As another example, at least the portion of the central core 18 located in the articulation region 14 may include a plurality of segments. As another example, the central core 18 may be the articulation insert described in U.S. patent application Ser. No. 12/436,087, filed on May 5, 2009 or U.S. patent application Ser. No. 12/477,065, filed on Jun. 2, 2009 (collectively referred to as the "Insert Documents"), both of which are herein incorporated by reference in their entirety. The central core 18 may include passages 20 defined generally longitudinally therein along which the articulation bands 16 are slidable. In this way, the passages 20 guide the articulation bands 16, particularly as articulation begins.

Referring to FIGS. 2 and 4, at least one articulation button 22 may be connected to the handle 12. Each articulation button 22 may be held within a knob 24. Optionally, the knob 24 may be fixed to the shaft 10, and the shaft 10 may be rotatable relative to the handle 12 such that rotation of the knob 24 causes the shaft 10, or at least the portion of the shaft 10 rigid and proximal to the articulation region 12, to rotate about its longitudinal axis relative to the handle 12. However, the knob 24 may be fixed relative to the handle 12 such that it does not rotate or move relative to the handle 12. As another example, the knob 24 may be omitted altogether.

Figure 5:
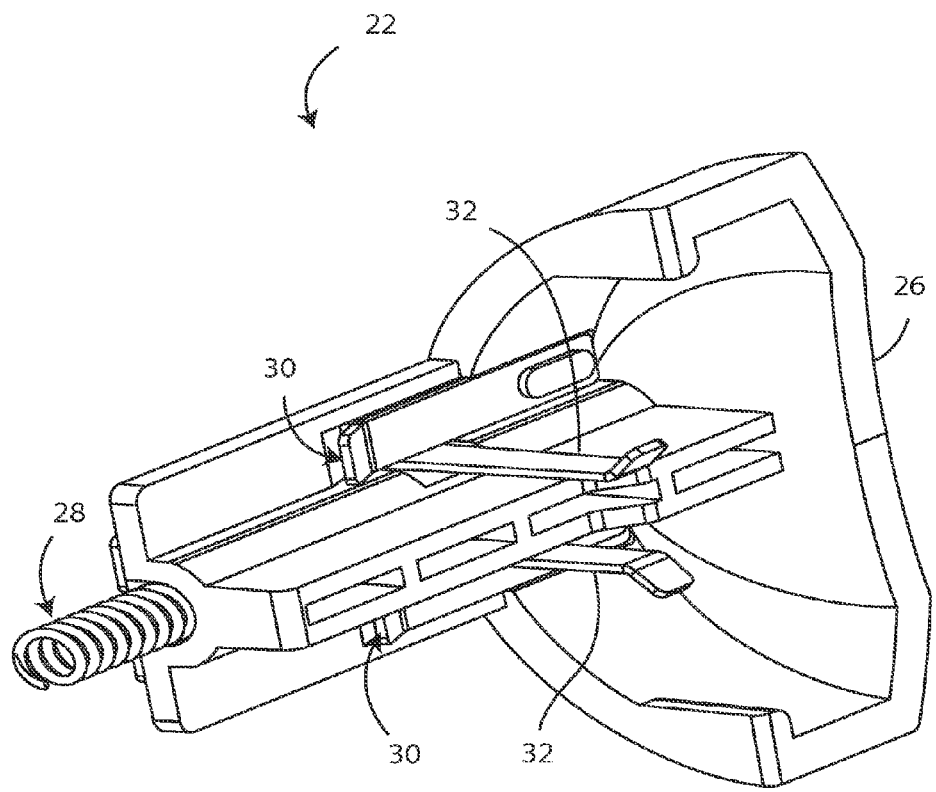
FIG. 5 is a perspective view of an articulation button of the articulation assembly of FIG. 4.
Figure 6:
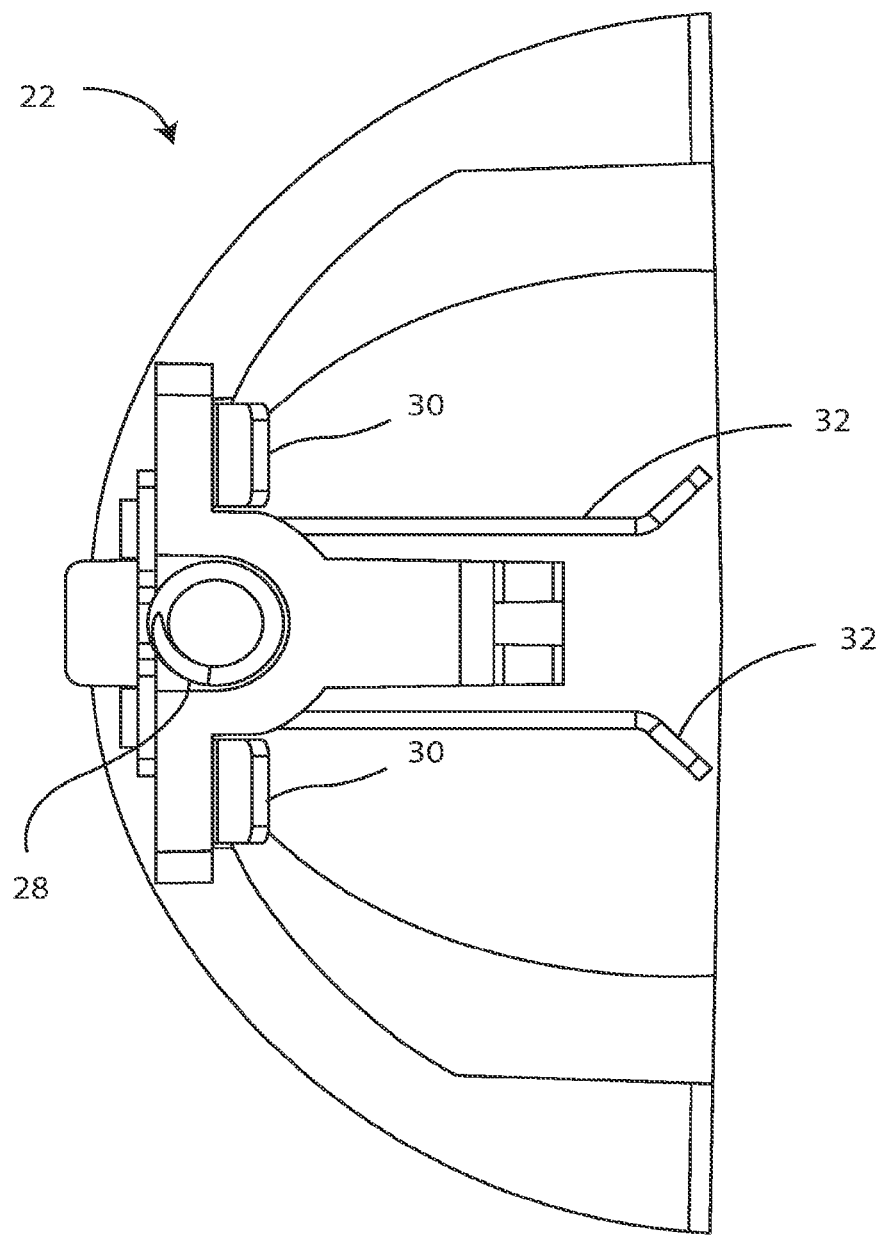
FIG. 6 is an end view of the articulation button of FIG. 5.

Referring also to FIGS. 5-6, each articulation button 22 may include a depression surface 26 that a user may press, as described in greater detail below. The depression surface 26 may be the most proximal surface of the articulation button 22, or may be any other suitable surface of the articulation button 22. A compression spring 28 may extend from the distal end of the articulation button 22, or from any other suitable portion of the articulation button 22. At least one pushing arm 30 may extend from the articulation button 22. Each pushing arm 30 may extend generally longitudinally, and flare inward near its distal end. As another example, at least one pushing arm 30 may be oriented or configured differently. At least one holding arm 32 may extend from the articulation button 22. As one example, each holding arm 32 may extending generally transversely, and flare vertically near its distal end. As another example, at least one holding arm 32 may be oriented or configured differently. Two articulation buttons 22 may be utilized: a left articulation button 22a and a right articulation button 22b, where "left" and "right" are defined relative to the longitudinal centerline of the shaft 10 viewed from the proximal end toward the distal end. Alternately, only a single articulation button 22 may be utilized. Where two pushing arms 30 and two holding arms 32 extend from each articulation button 22, optionally only one of each arm 30, 32 may be used by each articulation button 20 to actually control articulation. By providing two arms 30, 32 on each articulation button 20, the same articulation button 20 can be flipped such that the same configuration of articulation button 20

Figure 7:
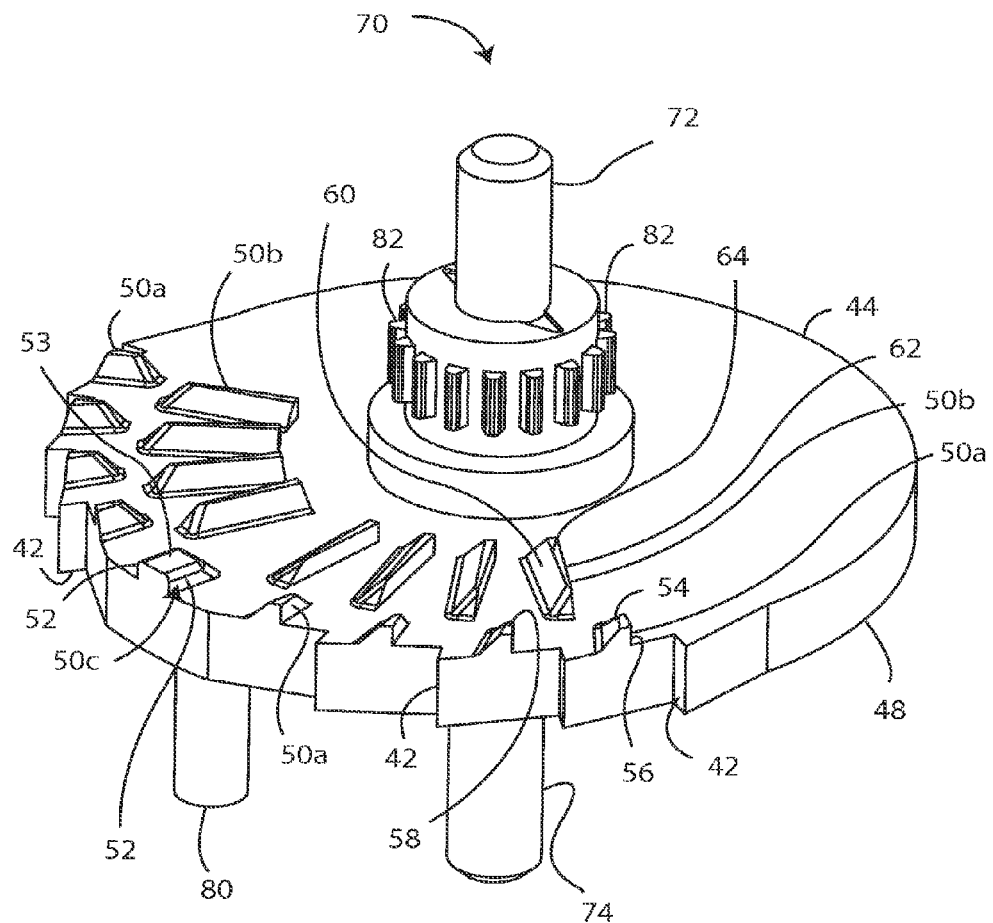
FIG. 7 is a perspective view of an articulation gear of the articulation assembly of FIG. 4.
Figure 8:
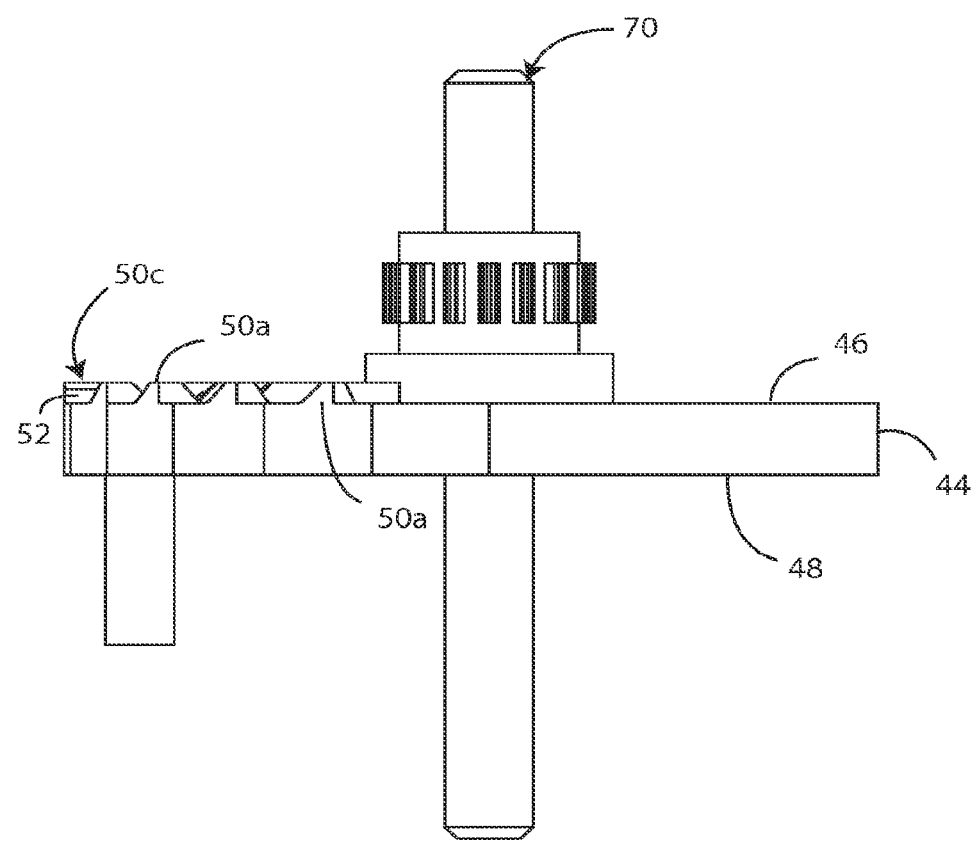
FIG. 8 is a side view of the articulation gear of FIG. 7.

Referring to FIGS. 4 and 7-8, an articulation gear 40 is shown. The gear 40 may be generally circular in shape. The articulation gear 40 may include outer teeth 42 defined along at least a portion of its outer perimeter 44. The gear 40 may include an upper surface 46 and a lower surface 48. At least one upper tooth 50 may extend upward from the upper surface 46. The upper teeth 50 may be organized into two separate arcs on the upper surface 46. The outer arc may include the outer, upper teeth 50a, and the inner arc may include the inner, upper teeth 50b. As another example, the upper teeth 50b may be omitted, and the upper teeth 50a may be organized into a single arc on the upper surface 46. The outer, upper teeth 50a may be organized into an arc, where a neutral tooth 50c occupies the center of the arc. The neutral tooth 50c may have two substantially vertical lateral walls 52. The upper surface 53 of the neutral tooth 50c may be substantially horizontal. On each side of the neutral tooth 50c, each outer, upper tooth 50a may include a ramp surface 54 sloping upward and away from the neutral tooth 50c. Each upper tooth 50a may include a vertical wall 56 opposite the ramp surface 54. The upper surface 58 of each upper tooth 50*a* may be substantially horizontal. As another example, each upper tooth 50*a* may be shaped in a different manner. The vertical wall 56 of each upper tooth 50*a*, and an arbitrary line parallel to the upper surface 46 of the gear 40 lying on the ramp surface 54 of each upper tooth 50*a*, may be substantially aligned with a radius of the gear 40. Alternately, at least one upper tooth 50*a* may be oriented differently on the upper surface 46 of the gear. The inner, upper teeth 50*b* may be organized into an arc as well, where the neutral tooth 50*c* is positioned further from the center of the gear 40 than the inner, upper teeth 50*b*. On each side of the neutral tooth 50*c*, each inner, upper tooth 50*b* may include a ramp surface 60 sloping upward and away from the neutral tooth 50*c*. Each inner, upper tooth 50*b* may include a vertical wall 62 opposite the ramp surface 60. The upper surface 64 of each upper tooth 50*a* may be substantially horizontal. As another example, each inner, upper tooth 50*b* may be shaped in a different manner. The vertical wall 56 of each upper tooth 50*a*, and an arbitrary line parallel to the upper surface 46 of the gear 40 lying on the ramp surface 54 of each upper tooth 50*a*, may be substantially angled relative to a radius of the gear 40, and thus out of alignment with a radius of the gear 40. Alternately, at least one upper tooth 50*a* may be oriented differently on the upper surface 46 of the gear 40.

Figure 9:
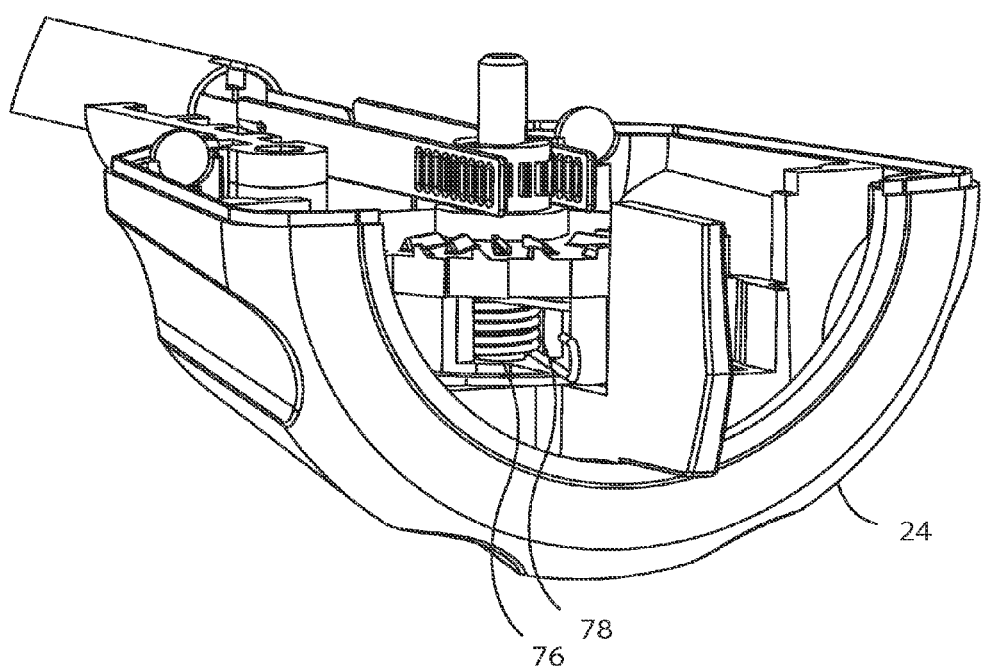
FIG. 9 is a perspective cutaway view of the articulation assembly of FIG. 4.

A spindle 70 may extend substantially perpendicular to the gear 40. The longitudinal centerline of the spindle 70 may extend through the geometric center of the gear 40. Alternately, the longitudinal centerline of the spindle 70 may be offset from the center of the gear 40. The spindle 70 may include an upper spindle 72 that extends upward from the upper surface 46 of the gear 40 and a lower spindle 74 that extends downward from the lower surface 48 of the gear 40. Referring also to FIG. 9, the spindle 70 is received in at least one receiver 76 defined in the knob 24. Advantageously, the upper spindle 72 and lower spindle 74 are each received in a separate receiver 76 in the knob 24. The gear 40 may be passive, and may be biased to a neutral position by a torsion spring 78. An anchor 80 may extend downward from the lower surface 48 of the gear 40, spaced radially apart from the lower spindle 74. The torsion spring 78 wraps around the spindle 70 and the anchor 80, which are spaced apart from one another, such that the torsion spring 78 biases the gear 40 to a neutral position.

Figure 10:
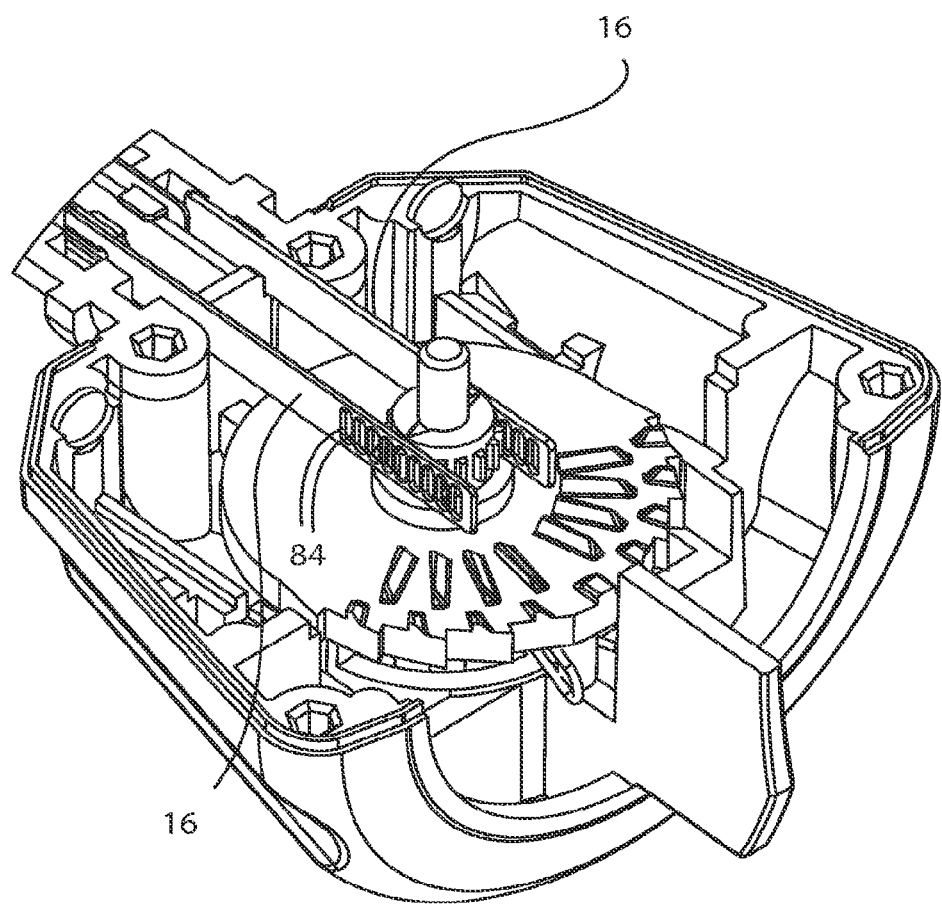
FIG. 10 is a perspective cutaway view of the articulation assembly of FIG. 4.

Spindle teeth 82 may extend radially outward from the spindle 70. As one example, the spindle teeth 82 extend radially outward from the upper spindle 72. As another example, the spindle teeth 82 may extend radially outward from any other portion of the spindle 70. The spindle teeth 82 may be generally rectangular, or may have any other suitable shape. For example, the spindle teeth 82 may be spiral or cylindrical. The spindle teeth 82 may be oriented such that their longer dimension is substantially vertical and their shorter dimension is horizontal. However, the spindle teeth 82 may be oriented in any other suitable direction or directions. Referring also to FIG. 10, apertures 84 may be defined through the articulation bands 16, near the proximal ends thereof. The apertures 84 may be sized and shaped to receive the spindle teeth 82 therein. As described in greater detail, rotation of the gear 40 about the spindle 70 causes the spindle teeth 82 to rotate and thereby cause differential motion of the articulation bands 16, urging one articulation band 16 proximally and the other articulation band 16 distally.

Figure 15:
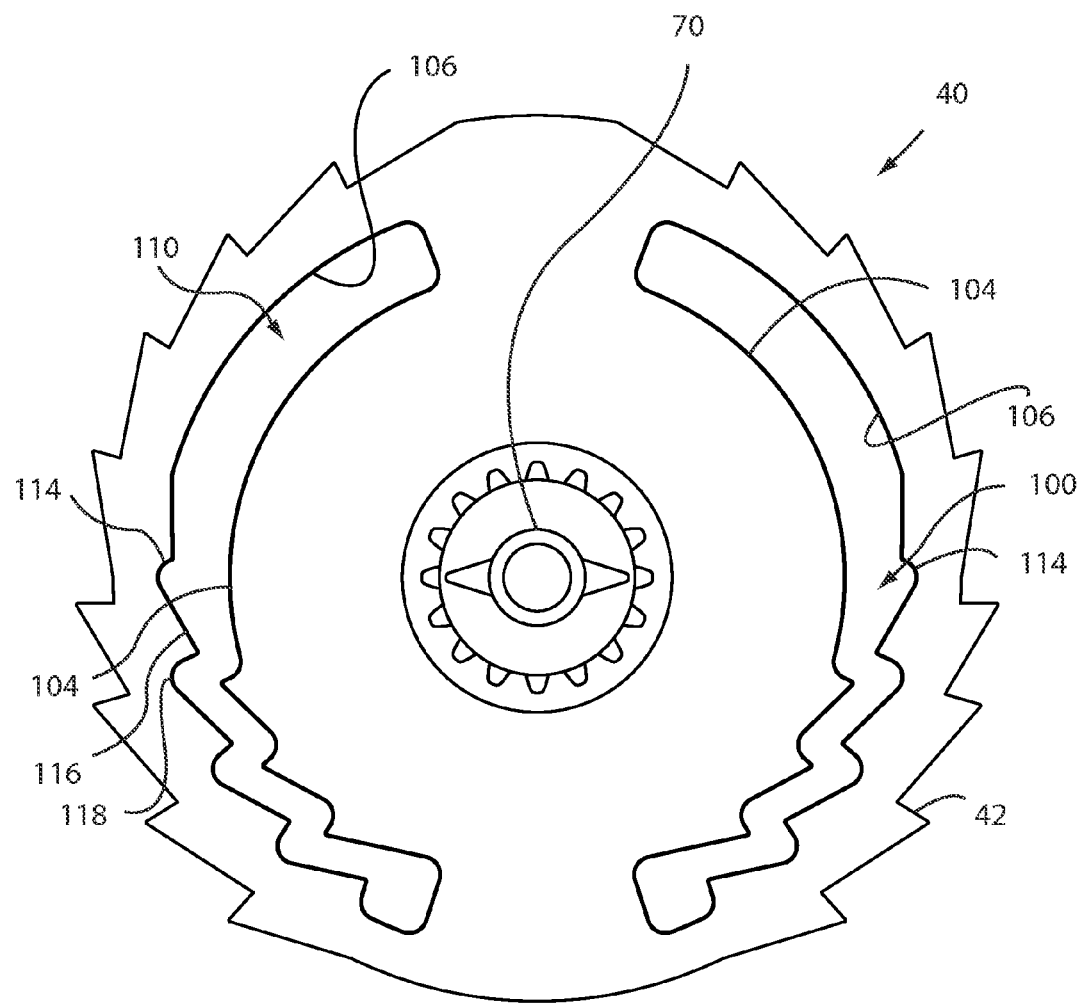
FIG. 15 is a top view of another embodiment of an articulation gear, including at least one cam path defined therein.
Figure 16:
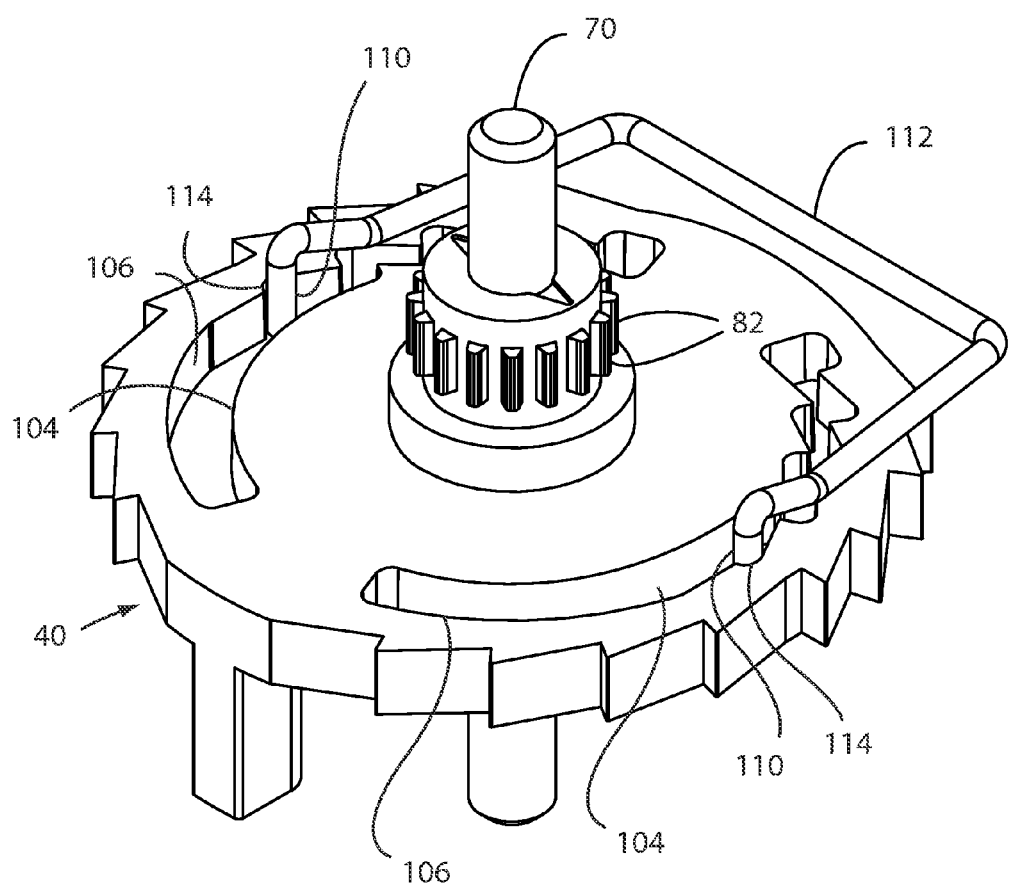
FIG. 16 is a perspective view of the articulation gear of FIG. 15, with a holder frame inserted into two cam paths.

As another example of an articulation gear 40, referring to FIGS. 15-16, the articulation gear 40 may omit the upper teeth 50 described above with regard to the previous example. Instead, the articulation gear 40 may include at least one cam path 100 defined therein. At least one cam path 100 may be a depression or similar recess defined in the articulation gear 40, with a lower surface 102. As another example, at least one cam path 100 may be defined completely through the articulation gear 40, such that it does not have a lower surface 102. Each cam path 100 may be a shape with a closed perimeter, and each cam path 100 may have a separate, closed perimeter. As another example, two or more cam paths 100 may be interconnected, such as for ease of manufacturing. Each cam path 100 may be generally curved at least partially about the spindle 70. Each cam path 100 may include an inner surface 104 closer to the spindle 70 and an outer surface 106 further from the spindle 70 than the inner surface 104. The outer teeth 42 of this example of the articulation gear 40 may be configured substantially as set forth above with regard to the previous example of the articulation gear 40.

Figure 17:
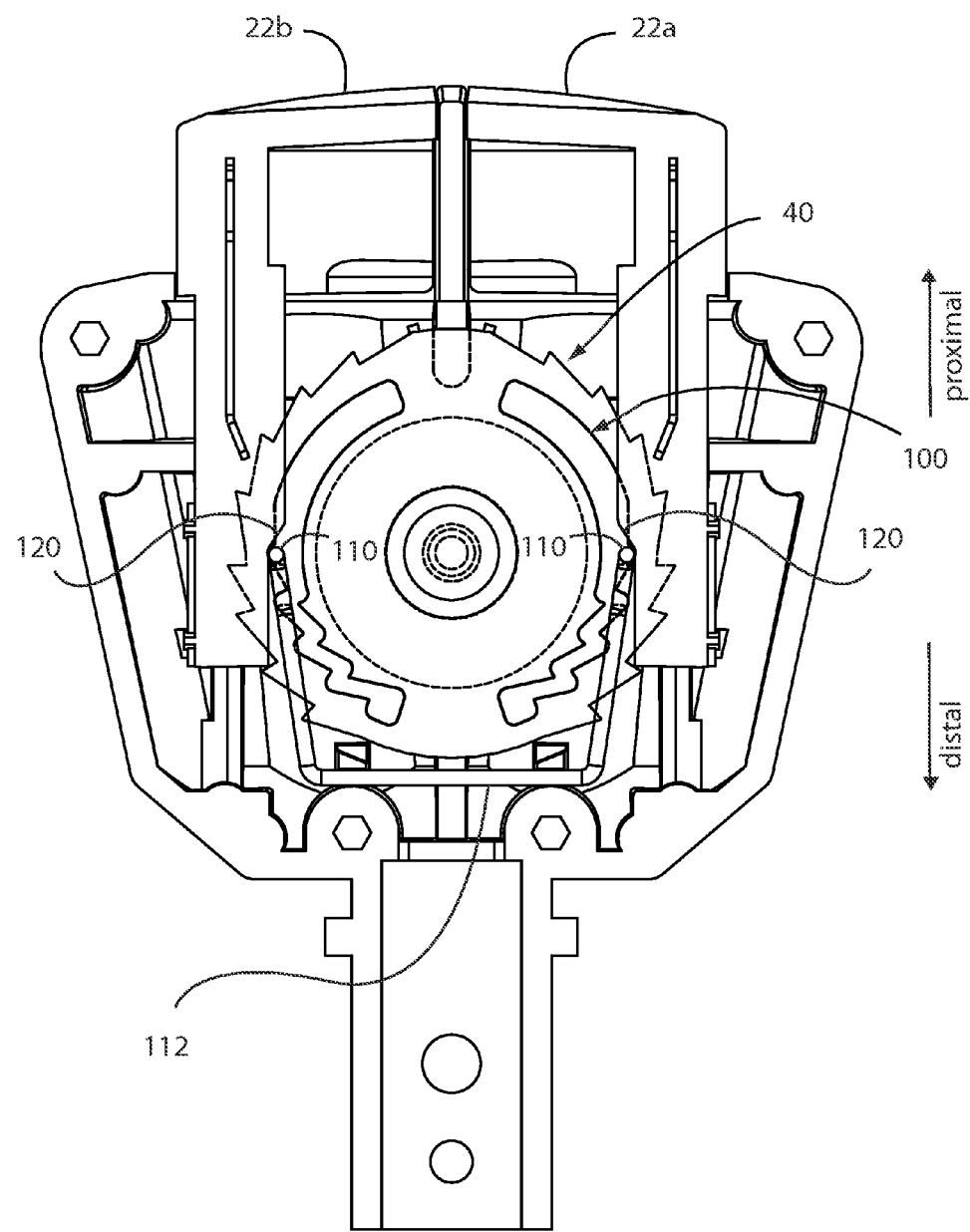
FIG. 17 is an upper cutaway view of an exemplary handle of a surgical tool, with the articulation gear of FIG. 15 held within the handle in a neutral position.

Referring also to FIGS. 15-17, one or more holder posts 110 may extend into each cam path 100. The holder posts 110 may be opposed ends, or other elements, of, a holder frame 112. In an initial, neutral position in which the end effector 4 is not articulated, each holder post 110 may reside in a first outer notch 114 in the outer surface 106 of the corresponding cam path 100. The holder posts 110 may be biased outward against the corresponding outer surfaces 106 of the cam paths 100, in any suitable manner. As one example, the holder frame 112 may be compressed inward in order to place the holder posts 110 in the cam paths 100 during manufacture, such that the holder frame 112 is sprung outward to bias the holder posts 110 outward toward the outer surfaces 106 of the cam paths 100. By biasing the holder posts 110 into corresponding first outer notches 114 in the outer surfaces 106 of the cam paths 100, the articulation gear 40 is held securely in place with little or no play.

Figure 18:
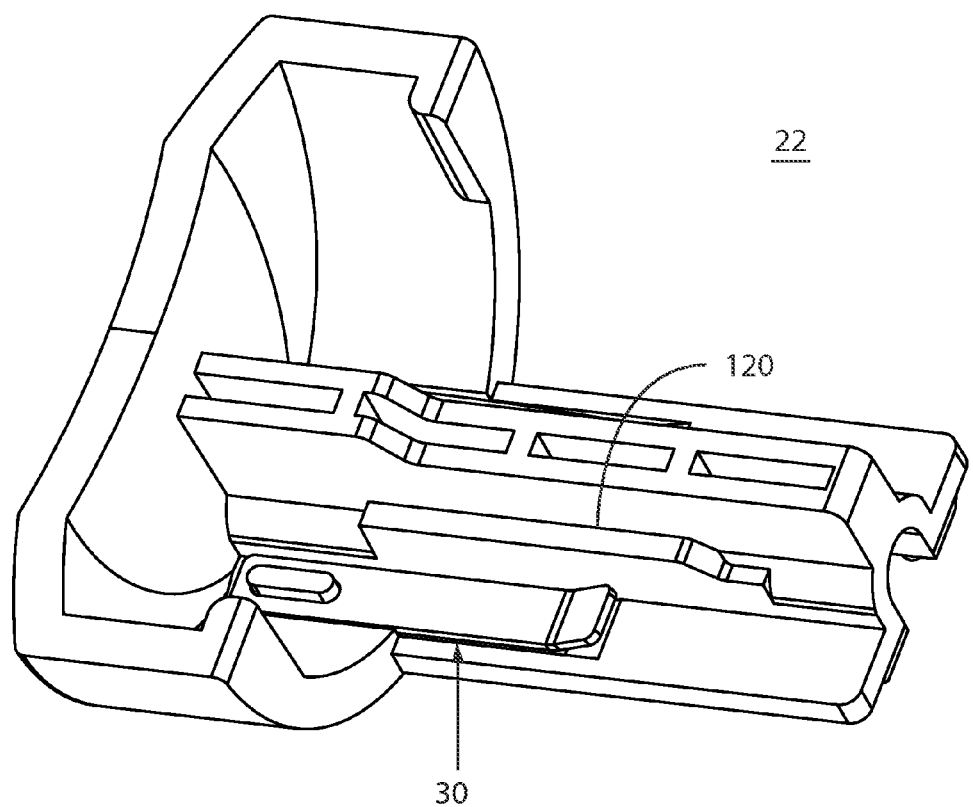
FIG. 18 is a perspective view of another exemplary articulation button.

Referring also to FIG. 18, the articulation buttons 22 utilized with the articulation gear 40 described immediately above with the cam path or paths 100 may be similar to the articulation buttons 22 described in the previous example, with a holder post deflection cam 120 defined on an inner surface 122 of each articulation button 22. The holder post deflection cam 120 may be located in proximity to and above the corresponding pushing arm 32 extending from the articulation button 22. Alternately, the holder post deflection cam 120 may be located in a different position on the articulation button 22. Where the articulation button 22 is utilized with the exemplary articulation gear 40 that utilizes at least one cam path 100 instead of upper teeth 50, the holding arms 32 may be omitted from the articulation button 22.

Figure 14:
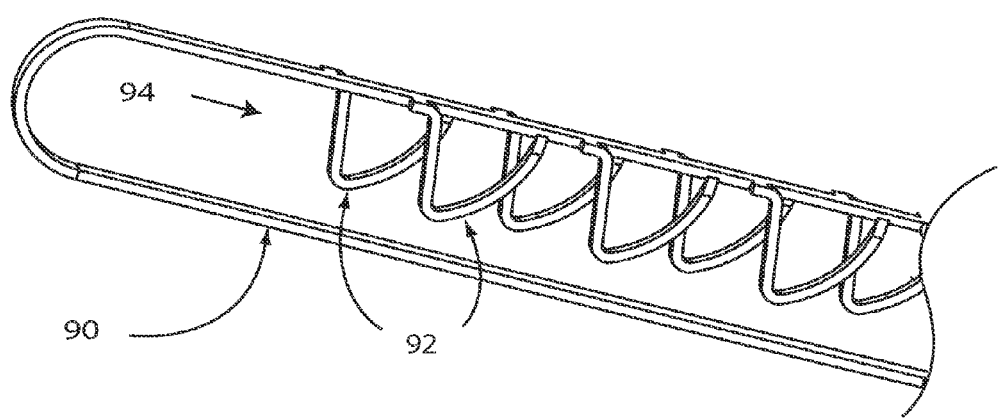
FIG. 14 is a perspective view of a feeder belt to which staples are frangibly connected.

Referring also to FIG. 14, a portion of at least one feeder belt 90 may extend from the shaft 10 into, or be positioned within, the end effector 4. The feeder belt 90 and its associated hardware may be as set forth in U.S. patent application Ser. No. 11/851,379, filed Sep. 6, 2007; U.S. patent application Ser. No. 11/956,988, filed Dec. 14, 2007; and U.S. patent application Ser. No. 12/263,171, filed Oct. 31, 2008 (the "Endocutter Documents"), which are herein incorporated by reference in their entirety. In the interest of brevity, the feeder belt 90 will not be described in detail herein. Each feeder belt 90 may be a long, narrow, thin strip of material from which one or more staples 92 extend. At least one staple 90 may be integral with the feeder belt 90, and frangibly connected to the feeder belt 90 at one end, with the other end of the staple being free. One row 94 of staples 92 may be located along each side of the feeder belt 90. Each feeder belt 90 may be movable relative to the end effector 4, as set forth in the Endocutter Applications, such that the end effector 4 can be actuated multiple times without the need to exchange cartridges or remove the end effector 4 from the patient between actuations. The end effector 4 may be configured generally as set forth in the Endocutter Documents, as one example, or may be configured differently.

Operation

The user possesses the surgical tool 2. The end effector 4 is placed in the body in proximity to its desired location relative to tissue. Advantageously, the end effector 4 is advanced through a trocar port or other minimally-invasive opening into the body. Where the end effector 4 includes a staple holder 8 and anvil 6, the end effector 4 may be opened such that at least the distal end of the anvil 6 is spaced apart from the staple holder 8 to allow tissue to be placed therebetween. However, the end effector 4 may be any other implement for treating tissue.

Referring also to FIG. 4, in order to articulate the end effector 4 relative to the shaft 10, the user actuates one of the articulation buttons 22. For clarity, the articulation of the end effector 4 leftward is described here. Articulation "leftward" refers to motion of the end effector 4 generally to the left as viewed by the user from the proximal toward the distal direction. In order to articulate the end effector 4 leftward, the user actuates the right articulation button 22b. The "right" articulation button 22b is the one on the right as viewed by the user from the proximal toward the distal direction. Actuation of the right articulation button 22b may be performed by pressing the right articulation button 22b generally distally. This exertion of force on the right articulation button 22b overcomes the bias exerted by the compression spring 28 against the right articulation button 22b in the proximal direction.

Figure 11:
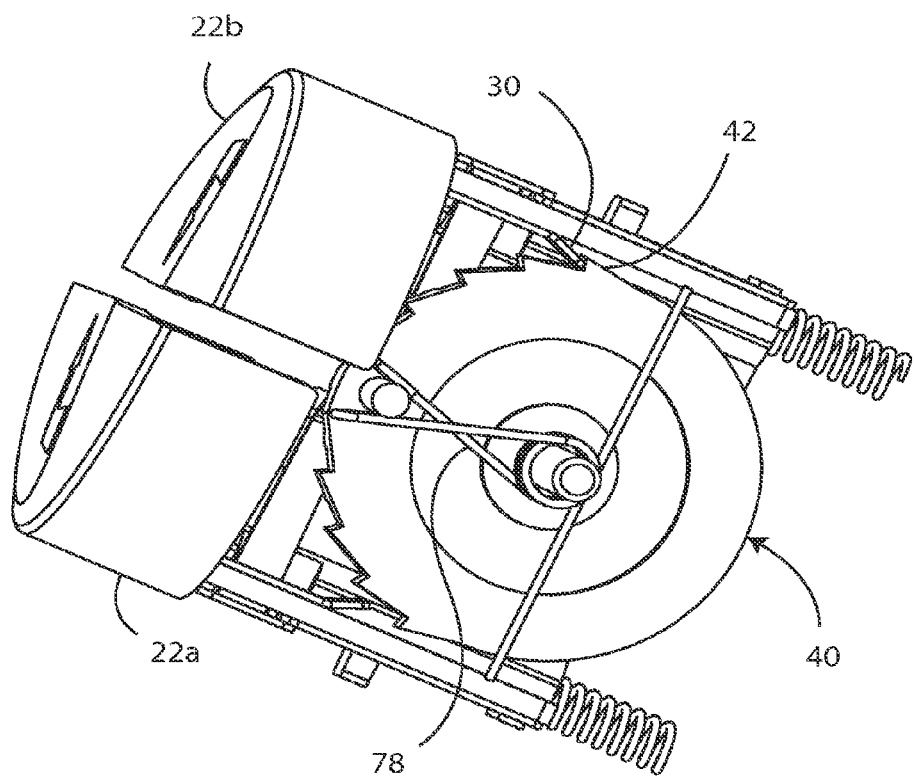
FIG. 11 is a perspective cutaway view of the articulation buttons and articulation gear during articulation through a first discrete angle.
Figure 12:
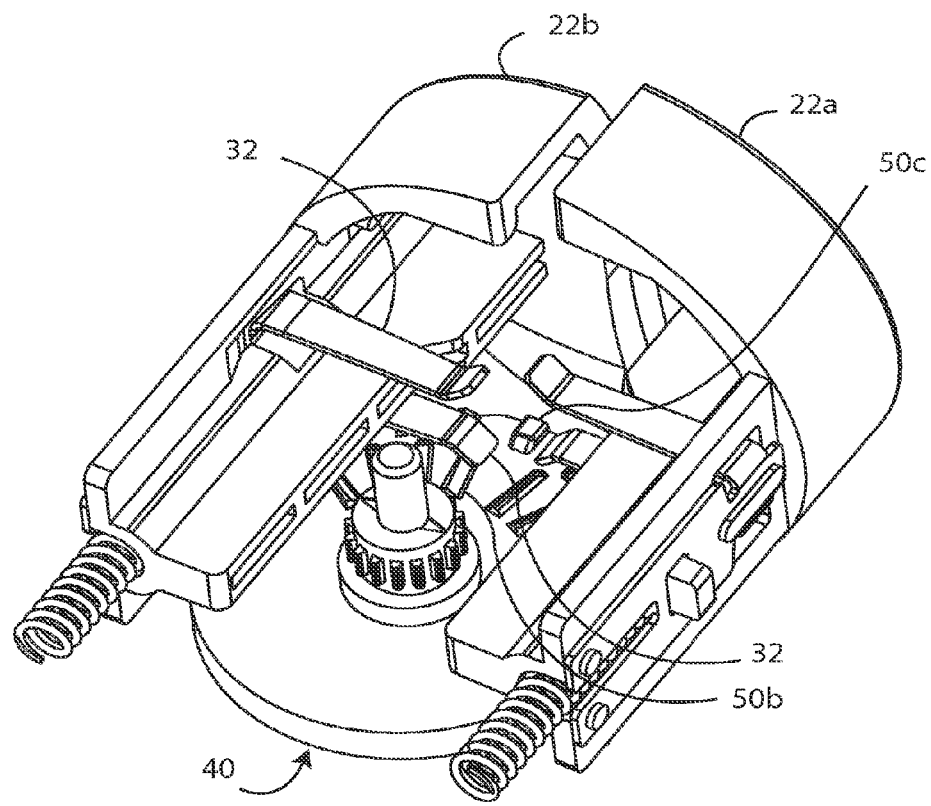
FIG. 12 is a perspective cutaway view of the articulation buttons and articulation gear at completion of articulation through a first discrete angle

Referring also to FIGS. 4-5, 7-8 and 10, as the right articulation button 22b advances distally relative to the knob 24 or other structure on the handle 12, the pushing arms 30 and holding arms 32 fixed to the right articulation button 22b advance distally as well. Referring also to FIG. 11, as the lower pushing arm 30 advances, it encounters and engages an outer tooth 42 of the articulation gear 40. Because the outer tooth 42 is laterally spaced from the spindle 70, the force exerted by the lower pushing arm 30 on the outer tooth 42 in the distal direction creates a moment about the spindle 70, causing the articulation gear 40 to rotate. As viewed from the underside of the articulation gear 40 in FIG. 11, the articulation gear 40 rotates in a clockwise direction. Consequently, as viewed from above, the articulation gear 40 rotates in a counterclockwise direction. As the right articulation button 22b continues its motion distally and the articulation gear 40 rotates, the outer, upper teeth 50a of the articulation gear 40 rotate with the articulation gear 40. Referring also to FIG. 12, during this rotation, the lower holding arm 32 of the left articulation button 22a slides up the ramp surface 54 of the outer, upper tooth 50a that is immediately to the left of the neutral tooth 50c, as viewed from the top. The lower holding arm 32 may flex as its distal end slides up the ramp surface 54, such that it snaps downward toward and/or against the upper surface 46 of the articulation gear 40 after it slides past the ramp surface 54 and the upper surface 58 of the outer, upper tooth 50a.

At such time, the right articulation button 22b has been depressed distally a sufficient amount, and may be released. The right articulation button 22b is urged proximally to its original position by the compression spring 28. As the right articulation button 22b moves proximally, the lower pushing arm 30 retracts out of engagement with the outer tooth 42 it had previously urged distally. However, the lower holding arm 32 of the left articulation button 22a holds the articulation gear 40 in place. The torsion spring 78 biases the articulation gear 40 in a direction opposite to the direction in which the articulation gear 40 had been rotated, such that the vertical wall 56 of the outer, upper tooth 50a adjacent to the tip of the lower holding arm 32 is biased against the lower holding arm 32. In this way, the lower holding arm 32 of the left articulation button 22a holds the articulation gear 40 in position.

During rotation of the articulation gear 40 as described above, the upper spindle 72 rotates with the articulation gear 40, as do the spindle teeth 82. The spindle teeth 82 engage apertures 84 of each articulation band 40. Rotation of the articulation gear 40 and upper spindle 72 in the direction described above—counterclockwise as viewed from the top—thus causes the right articulation band 16 to advance distally, and the left articulation band 16 to retract proximally. The left articulation band 16 may be fixed to the left side of the end effector 4, and the right articulation band 16 may be fixed to the right side of the end effector 4. As a result, that distal force exerted on the right side of the end effector 4 by the right articulation band 16, and the proximal force exerted on the left side of the end effector 4 by the left articulation band 16, cause a moment that bends the articulation region 12 laterally leftward. Bending of the articulation region 10 relative to the shaft 6 to change the orientation of the end effector 4 is referred to as "articulating" the end effector 4. In response to a complete depression and release of the right articulation button 22b, the end effector 4 has thus articulated leftward in a discrete increment. That is, the angular spacing between the outer, upper teeth 50a along the circumference of the articulation gear 40 defines increments in which the articulation gear 40 rotates, and in turn those increments of rotation are converted to increments of articulation of the end effector 4. Put another way, each actuation of an articulation button 22 causes the end effector 4 to articulate a discrete and known amount.

Figure 13:
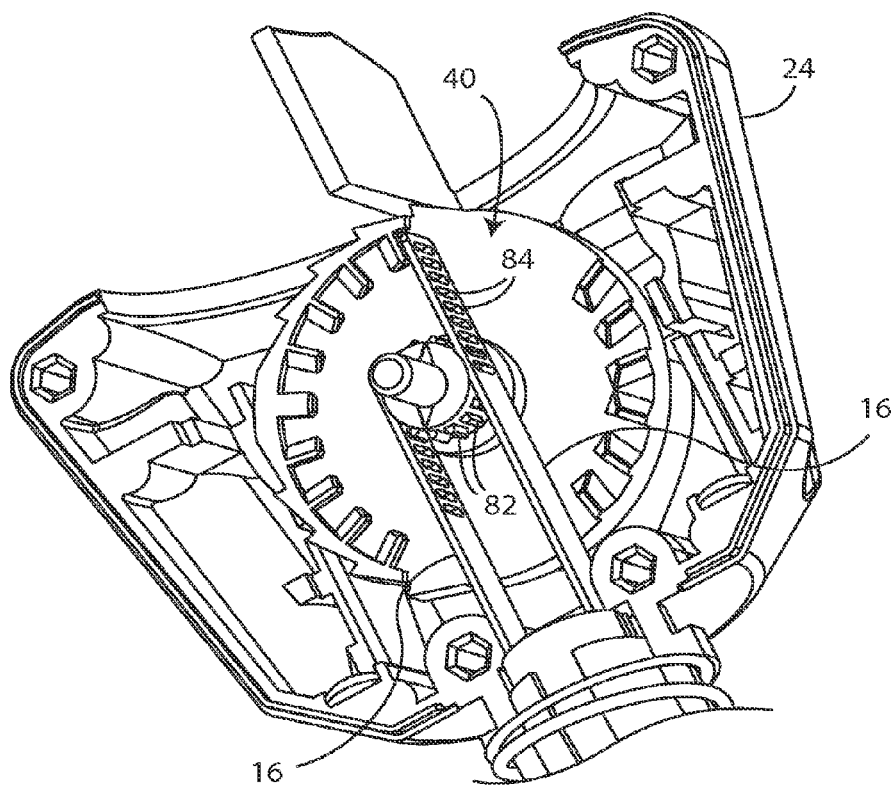
FIG. 13 is a perspective cutaway view of the articulation assembly at the limit of articulation.

If further articulation of the end effector 4 is desired, the user may actuate the right articulation button 22b again. If so, the articulation gear 40 rotates as described above, and the end effector 4 articulates by another discrete amount, which may be the same as or different then the previous discrete amount. The end effector 4 may step through several discrete steps of articulation as a result of several depressions of the right articulation button 22b. Referring also to FIG. 13, the end effector 4 may continue to be articulated further leftward until the lower holding arm 32 of the left articulation button 22a is holding the last outer, upper tooth 50a. As one example, an additional actuation of the right articulation button 22a simply results in no further articulation of the end effector 4, because there is not another outer, upper tooth 50a for the lower holding arm 32 to engage. As another example, depression of the left articulation button 22a at this point (or at an earlier point in the articulation of the end effector 4) moves the lower holding arm 32 out of engagement with the outer, upper tooth 50a that it had previously engaged, and places the distal end of the lower holding arm 32 at a location inward toward the spindle 70 such that the distal end of the lower holding arm 32 is located radially inward from each of the outer, upper teeth 50a. As a result, the torsion spring 78 urges the articulation gear 40 back to its neutral position, and consequently the end effector 4 returns to its original, non-articulated position in which it is substantially longitudinally aligned with the shaft 10.

As another example, where the articulation gear 40 includes a set of inner, upper teeth 50b, the articulation gear 40 steps in reverse toward the neutral position upon depression of the left articulation button 22a. Referring also to FIGS. 4, 7 and 10, as the left articulation button 22a is depressed, the distal end of the lower holding arm 32 moves inward toward the spindle 70, out of engagement with the outer, upper tooth 50a it had previously engaged and held. As a result, the torsion spring 78 urges the articulation gear 40 back toward its neutral position. However, the distal end of the lower holding arm 32 encounters an inner, upper tooth 50b as the articulation gear 40 moves toward that neutral position. The angular force exerted by the torsion spring 78 may then hold the inner, upper tooth 50b against the lower holding arm 32, such that the articulation gear 40 rotates a discrete increment less than the discrete increments that it rotated during the previous articulation of the end effector 4 leftward. Consequently, the end effector 4 articulates rightward by a discrete angle that is less than the discrete angles through which it had articulated leftward. Alternately, the inner, upper tooth 50b simply arrests the motion of the articulation gear 40, and the lower holding arm 32 then slides proximally into engagement with the next outer, upper tooth 50a. In this way, the articulation gear 40 rotates a discrete increment the same as the discrete increments in which it had rotated previously, and the end effector 4 articulates rightward by a discrete angle substantially the same as the discrete angles through which it had rotated during the previous articulation of the end effector 4 leftward.

For conciseness and clarity, articulation of the end effector 4 in the left direction using the right articulation button 22b has been described above. Articulation of the end effector 4 in the right direction, using the left articulation button 22a, is performed substantially as set forth above, in a reversed, mirror-image manner. Optionally, the shaft 10 may be rotatable relative to the handle 12, as set forth in commonly-assigned U.S. Pat. No. 7,918,376, which is herein incorporated by reference in its entirety. In this manner, the end effector 4 can be rotated as well as articulated left and right, in order to place the end effector 4 in a desired position within a patient.

As another example, a single articulation button 22 may be provided, rather than the two articulation buttons 22a, 22b described above. If so, the neutral position of the articulation gear 40 is a rotation all the way to one side, such that the end effector 4 is fully articulated laterally in the neutral position. The end effector 4 then may be articulated in discrete increments from that neutral position, utilizing only a single articulation button 22.

Turning to the exemplary articulation gear 40 that includes at least one cam path 100 defined therein, instead of upper teeth 50 defined thereon, articulation may be performed in a similar but different manner. Referring to FIGS. 15-18, in order to articulate the end effector 4 relative to the shaft 10, the user actuates one of the articulation buttons 22. For clarity, the articulation of the end effector 4 rightward is described here. Articulation "rightward" refers to motion of the end effector 4 generally to the right as viewed by the user from the proximal toward the distal direction. In order to articulate the end effector 4 leftward, the user actuates the left articulation button 22a. The "left" articulation button 22a is the one on the left as viewed by the user from the proximal toward the distal direction. Actuation of the left articulation button 22a may be performed by pressing the left articulation button 22a generally distally. This exertion of force on the left articulation button 22a overcomes the bias exerted by the compression spring 28 against the left articulation button 22a in the proximal direction.

Figure 19:
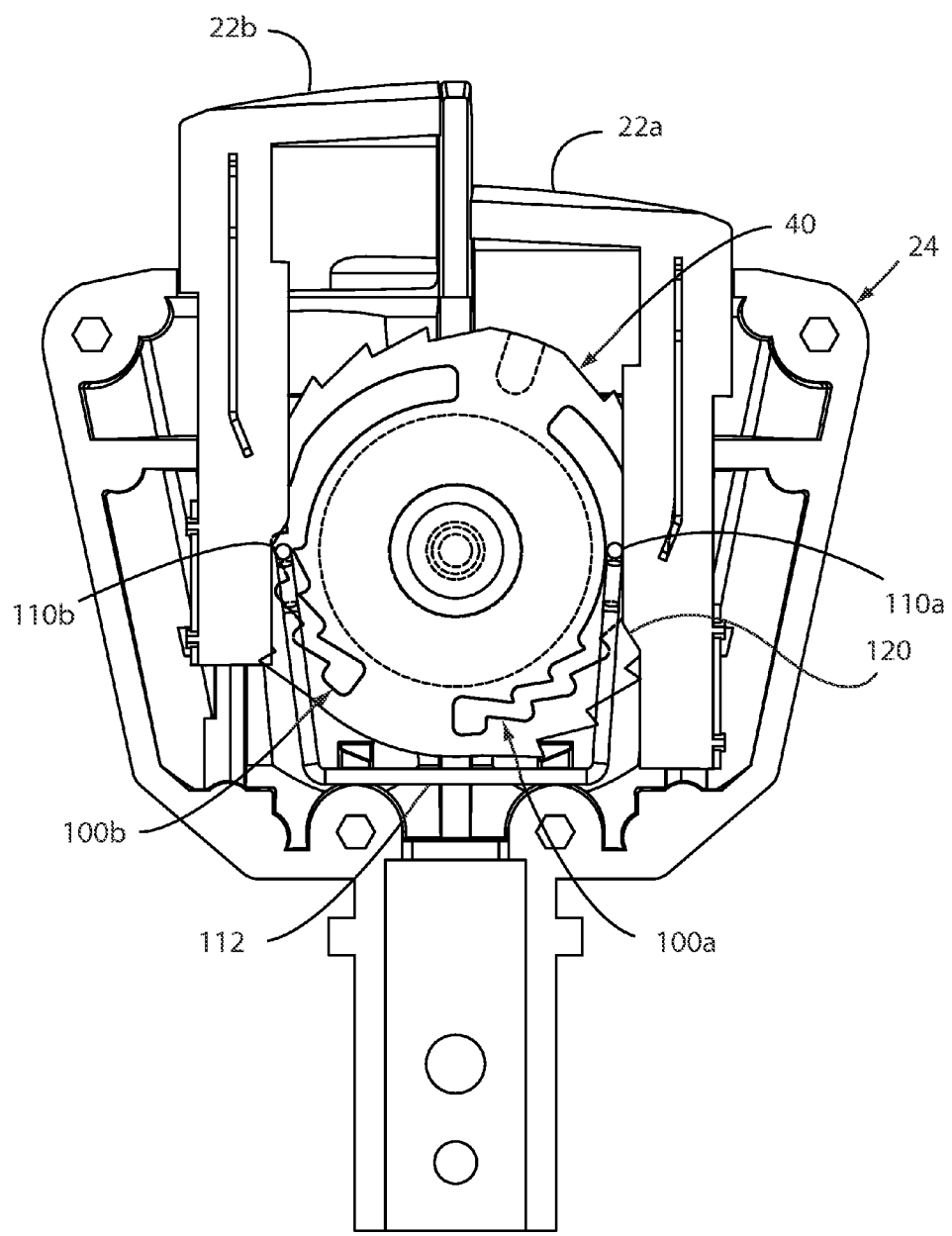
FIG. 19 is an upper cutaway view of an exemplary handle of a surgical tool, with the articulation gear of FIG. 15 held within the handle, and the left articulation button depressed.

Referring also to FIG. 19, as the left articulation button 22a advances distally relative to the knob 24 or other structure on the handle 12, the pushing arm 30 fixed to the left articulation button 22a advances distally as well. As the pushing arm 30 advances, it encounters and engages an outer tooth 42 of the articulation gear 40. Because the outer tooth 42 is laterally spaced from the spindle 70, the force exerted by the pushing arm 30 on the outer tooth 42 in the distal direction creates a moment about the spindle 70, causing the articulation gear 40 to rotate. As viewed from the upper side of the articulation gear 40 in FIG. 19, the articulation gear 40 rotates in a clockwise direction. As the articulation gear 40 rotates, some of the energy of motion of the left articulation button 22a is stored in the torsion spring 78, which is thereby biased toward the neutral position of the articulation gear 40 as a result of that energy storage.

Figure 20:
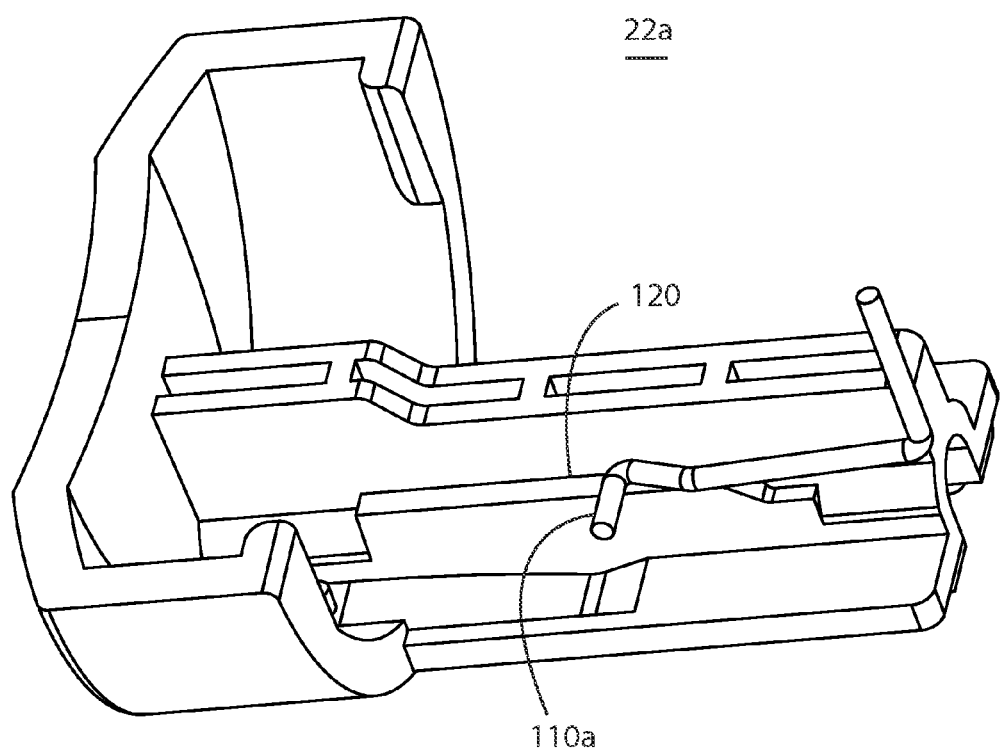
FIG. 20 is a perspective view of the articulation button of FIG. 18, engaging a holder post.

As the articulation gear 40 rotates, each holder post 110 moves in the corresponding cam path 100 defined in the articulation gear 40. The holder post 110 closest to the left articulation button 22a may be referred to as the left holder post 110a, and the corresponding cam path 100 may be referred to as the left cam path 100a. The holder post 110 closest to the right articulation button 22b may be referred to as the right holder post 110b, and the corresponding cam path 100 may be referred to as the right cam path 100b. As the left articulation button 22a moves distally, the distal end of the holder post deflection cam 120 encounters the left holder post 110a, urging that left holder post 110a inward, as seen in FIG. 20. In this way, the holder post deflection cam 120 urges the left holder post 110a out of engagement with the corresponding first outer notch 114 in which that left holder post 110 had initially resided. As seen in FIG. 19, as the articulation gear 40 rotates clockwise, the left holder post 110a—now out of engagement with the first outer notch 114—can move substantially freely into the portion of the cam path 100 located above the left holder post 110a on the page. That is, the left holder post 110a is biased toward the outer surface 106 of the left cam path 100a, and that outer surface 106 of the left cam path 100a is smooth on the portion of the left cam path 100a that the left holder post 110a encounters during clockwise rotation of the articulation gear 40 from a neutral position (which is during rightward articulation of the end effector 4).

Additionally, as the articulation gear 40 rotates clockwise, the right holder post 110b remains biased outward toward the outer surface 106 of the right cam path 100b. Because the right articulation button 22b has not moved and does not move distally during rightward articulation, the holder post deflection cam 120 on the right articulation button 22b does not move, such that it does not urge the right holder post 110b out of engagement with its corresponding first outer notch 114. However, as the articulation gear 40 rotates clockwise, the right holder post 110b slides against the first ramp 116 defined in the outer surface 106 of the cam path 100b that is located distal to the first outer notch 114. That is, engagement between the right holder post 11b and the first outer notch 114 prevents counterclockwise rotation of the articulation gear 40, but allows clockwise rotation of the articulation gear 40 by allowing the right holder post 110b to slide along the first ramp 116. The first ramp 116 may be angled toward the spindle 70, such that as the right holder post 110b slides along the first ramp 116, the first ramp 116 also urges the right holder post 110b inward toward the longitudinal centerline of the knob 24. As the articulation gear 40 continues to rotate counterclockwise, under the influence of engagement between the pushing arm 30 of the left articulation button 22a and an outer tooth 42 of the articulation gear 40, the right holder post 110b slides off the proximal end of the first ramp 116 and snaps into the second outer notch 118. The second outer notch 118 is located in the outer surface 106 of the cam path 100b, counterclockwise from the first outer notch 114. The length of the first ramp 116 is related to the amount of clockwise motion of the articulation gear 40, which in turn is related to the length of distal travel of the left articulation button 22a. The length of the first ramp 116 corresponds to the full stroke of the left articulation button 22a such that a full stroke (i.e., complete depression) of the left articulation button 22a causes the right holder post 11b to move from the first outer notch 114 to the second outer notch 118.

At this point, the left articulation button 22a is released, moving the left holder post 110a back into engagement with a smooth section of the outer surface 106 of the cam path 100a. The right holder post 110b is engaged with the second outer notch 118. This engagement, coupled with the bias of the torsion spring 78 in the counterclockwise direction, holds the articulation gear 40 in position, such that the end effector 4 has been articulated through a discrete angle and is now held at that angle. As set forth above, engagement between the spindle teeth 82 and the articulation bands 16 causes that articulation of the end effector 4.

Figure 21:
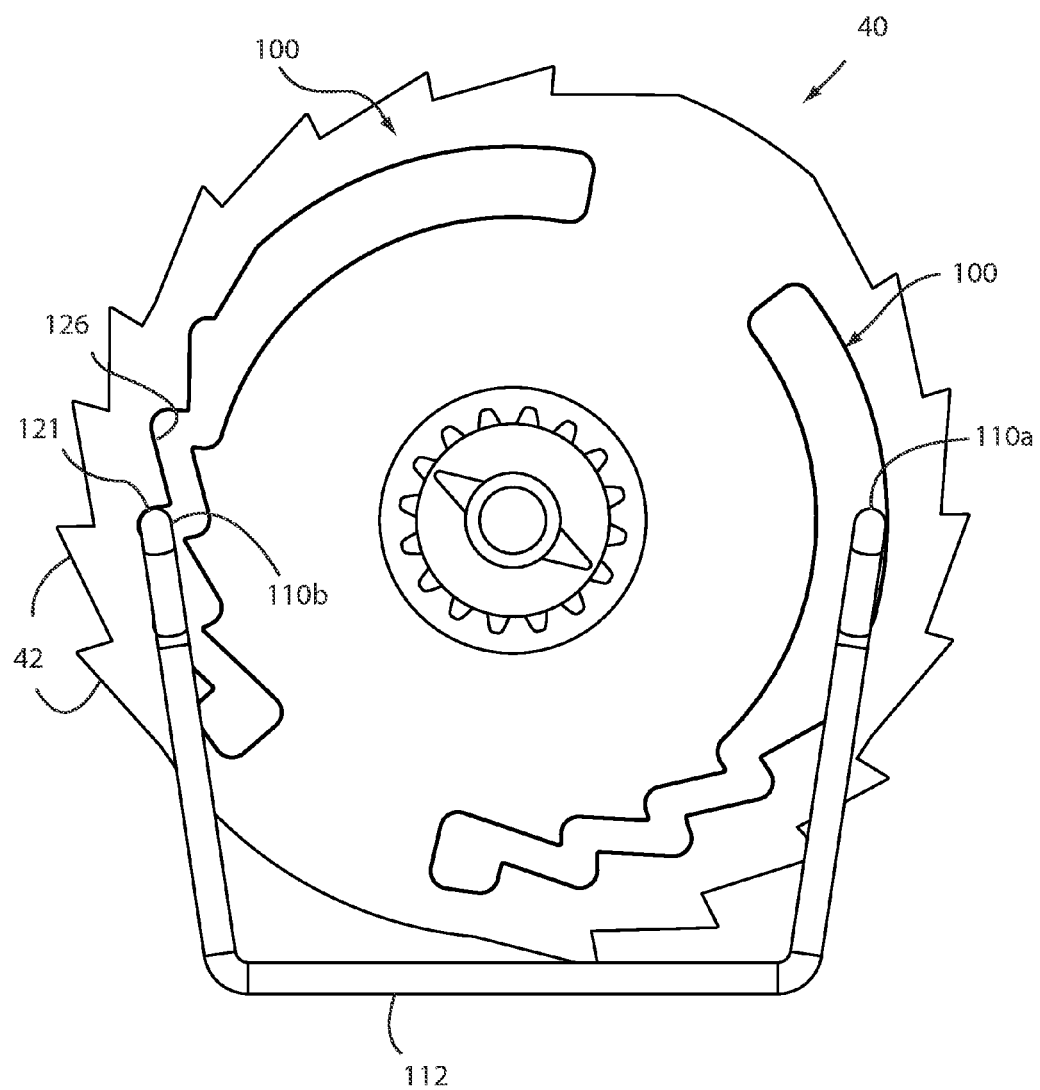
FIG. 21 is a top view of the articulation gear and holder frame of FIG. 16 in a second discrete position.
Figure 22:
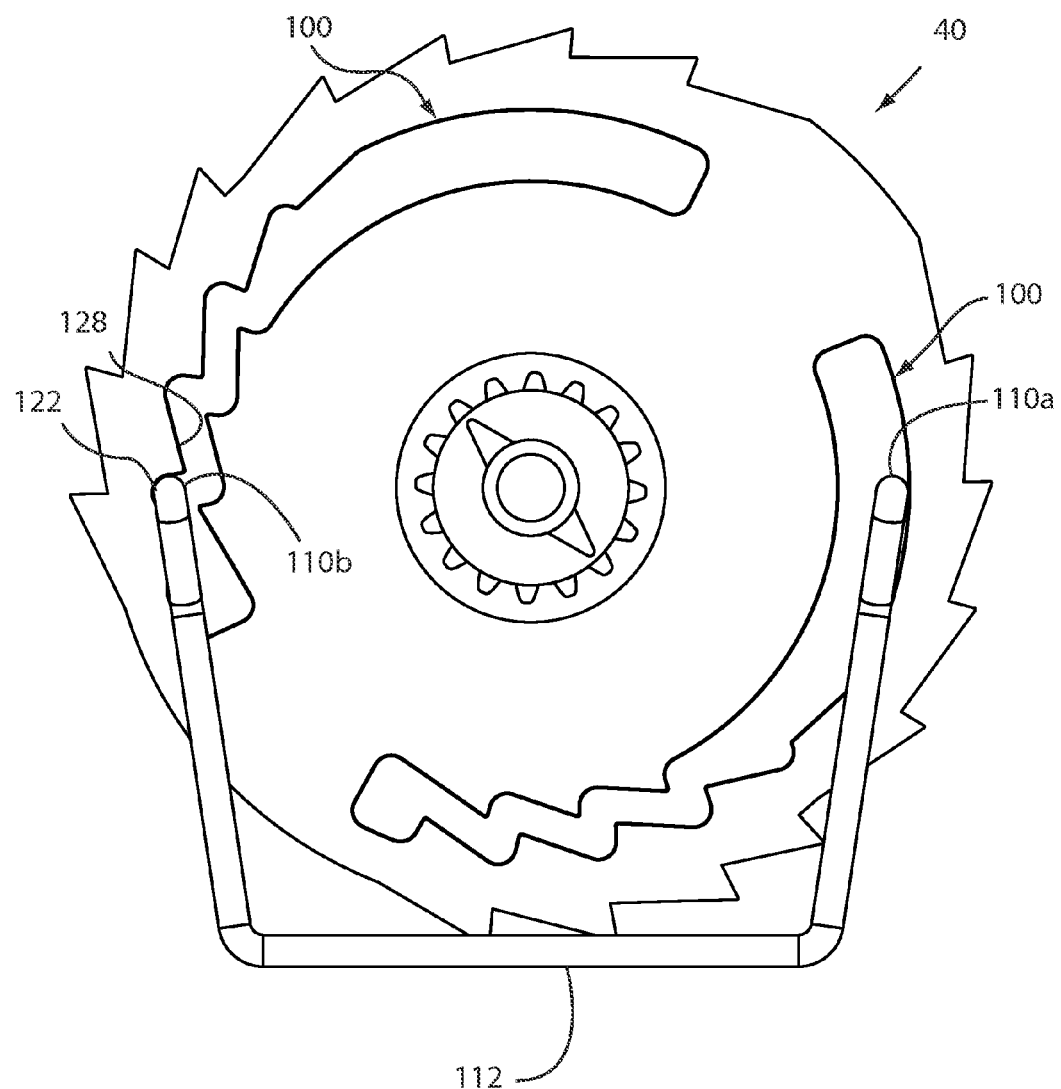
FIG. 22 is a top view of the articulation gear and holder frame of FIG. 16 in a third discrete position.
Figure 23:
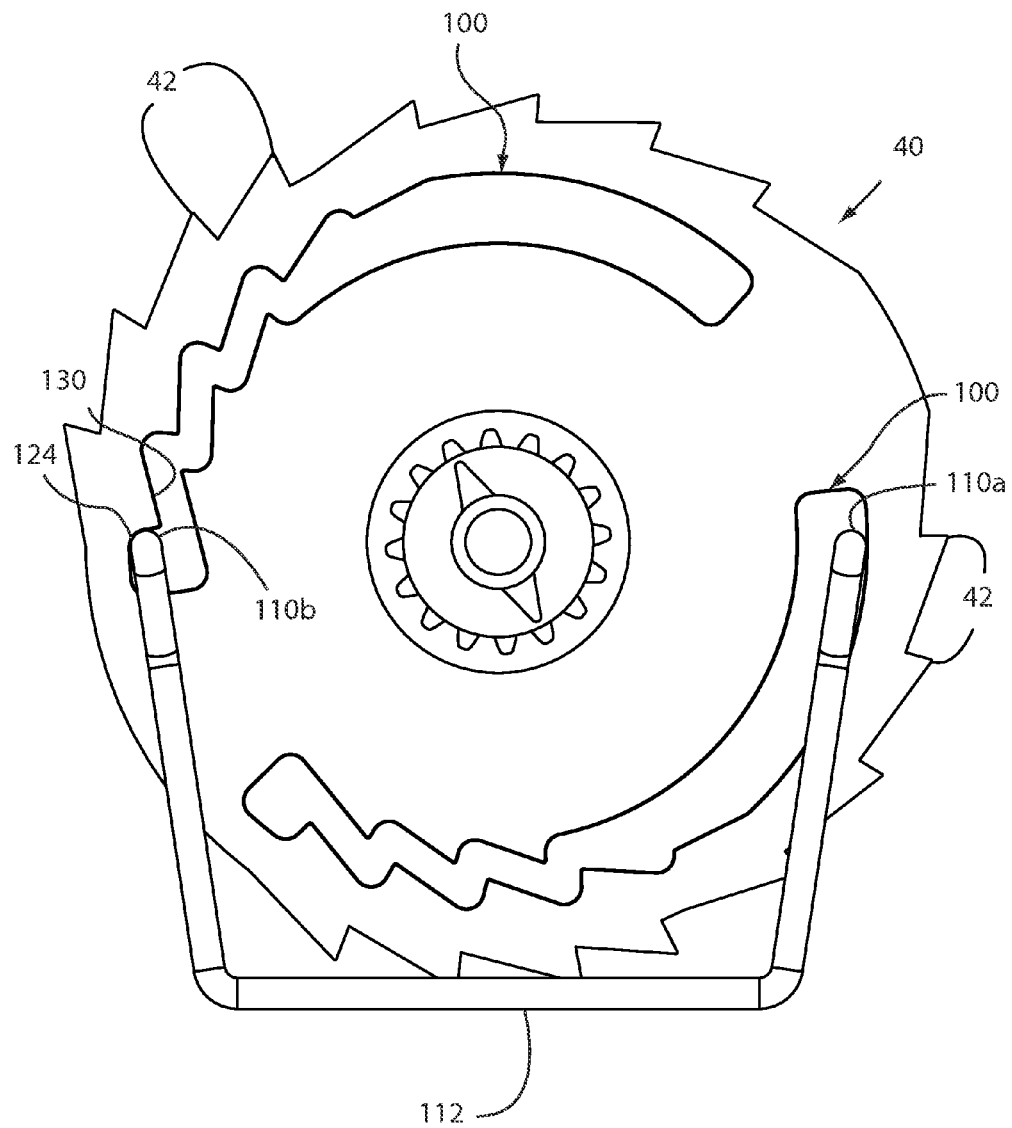
FIG. 23 is a top view of the articulation gear and holder frame of FIG. 16 in a fourth discrete position.

Articulation of the end effector 4 through successive additional rightward angular iterations, if desired, may be accomplished by repeating what is set forth above. Referring to FIGS. 21-23, successive depressions of the left articulation button 22a cause the left holder post 110a to slide along a smooth portion of the outer surface 106 of the cam path 100a, and cause the right holder post 110b to slide successively along ramps 126, 128, 130 to outer notches 121, 122, 124. Of course, more or fewer ramps and/or notches may be provided in order to provide for more or less articulation, and/or to provide for larger or smaller discrete angles of articulation of the end effector 4.

When the articulation gear 40 has reached the point of rotation at which the cam path 100b cannot rotate clockwise any further due to engagement of the right holder post 110b with a final notch 124 and/or with an end of the cam path 100b, the articulation gear 40 cannot rotate further, and articulation rightward is complete. It will be apparent from the description above that articulation of the end effector 4 leftward happens as set forth above, but in a mirror-image manner.

Figure 24:
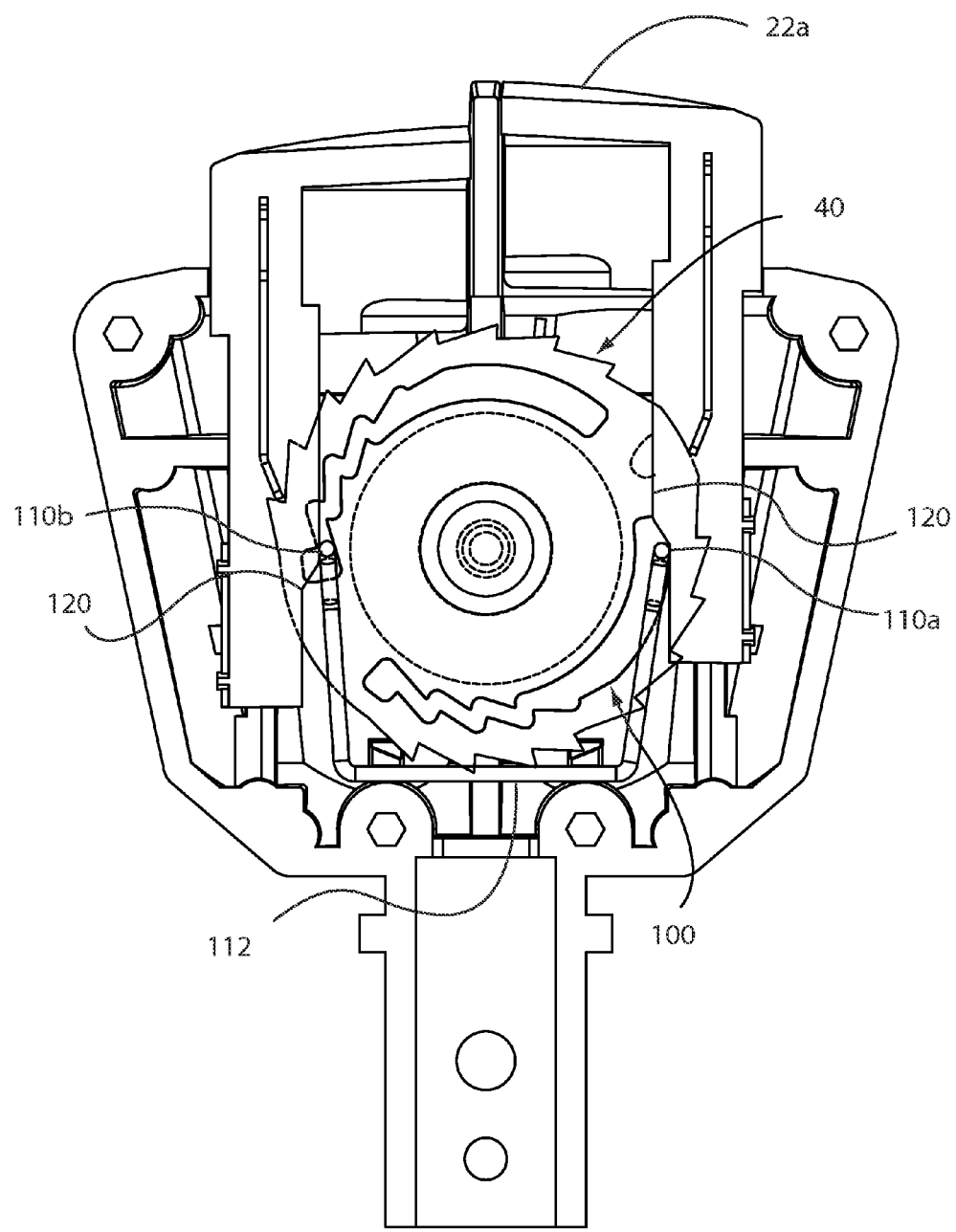
FIG. 24 is an upper cutaway view of an exemplary handle of a surgical tool, with the articulation gear of FIG. 15 held within the handle, and the right articulation button depressed to begin articulation return.

The user may wish to return the end effector 4 in the opposite, leftward direction at that time. Of course, the user may wish to articulate the end effector 4 leftward before the end effector 4 reaches a point of rightmost articulation. In order to articulate the end effector 4 leftward after at least one discrete articulation rightward, the user depresses the right articulation button 22b. Referring also to FIG. 24, as the right articulation button 22b advances distally relative to the knob 24 or other structure on the handle 12, the pushing arm 30 fixed to the right articulation button 22b advances distally as well. As the pushing arm 30 advances, it encounters and engages an outer tooth 42 of the articulation gear 40. Because the outer tooth 42 is laterally spaced from the spindle 70, the force exerted by the pushing arm 30 on the outer tooth 42 in the distal direction creates a moment about the spindle 70, causing the articulation gear 40 to rotate. As viewed from the upper side of the articulation gear 40 in FIG. 19, the articulation gear 40 rotates in a counterclockwise direction. As the articulation gear 40 rotates, some of the energy of motion of the left articulation button 22a is released from the torsion spring 78, which is biased toward the neutral position of the articulation gear 40 as a result of stored energy within the spring 78.

As the articulation gear 40 rotates, each holder post 110 moves in the corresponding cam path 100 defined in the articulation gear 40. Referring also to FIG. 23, the left holder post 110a was not previously engaged with an outer notch, and slides along a smooth portion of the outer surface of the cam path 100a as the articulation gear 40 rotates counterclockwise. As the right articulation button 22b moves distally, the distal end of the holder post deflection cam 120 encounters the right holder post 110b, urging that right holder post 110b inward, as seen in FIG. 24. In this way, the holder post deflection cam 120 urges the right holder post 110b out of engagement with the corresponding outer notch 124 in which that right holder post 110b had previously resided. (The articulation described herein, returning from a previous articulation in the other direction, is performed the same way regardless of which outer notch has engaged the right holder post 110b; the discussion with regard to the final outer notch 124 is for clarity.) As the articulation gear 40 rotates counterclockwise, the right holder post 110b is held inward from the distal end of the ramp 130 located proximal to the outer notch 124. As a result, that right holder post 110b slides between the ramp 130 and the inner surface 104 of the cam path 100b. In this way, the holder post deflection cam 120 engages the right holder post 110b to allow counterclockwise motion of the articulation gear 40. As the articulation gear 40 continues to rotate counterclockwise under the influence of engagement between the pushing arm 30 of the right articulation button 22a and an outer tooth 42 of the articulation gear 40, the right holder post 110b moves into engagement with the outer notch 122 located clockwise from the previous outer notch 124. That engagement prevents further counterclockwise motion of the articulation gear 40, such that the articulation back toward the neutral position is stopped, and holding the articulation gear 40 in position. The position occupied by the end effector 4 may be the previous discrete angular position occupied by the end effector 4 prior to the return articulation described immediately above. The end effector 4 has been articulated through a discrete angle and is now held at that angle. The right articulation button 22b is released; however, the right holder post 110b is already engaged in a notch in the outer surface 106 of the cam path 100b, such that removal of any bias inward of the right holder post 110b does not cause it to move relative to the cam path 100b.

Articulation of the end effector 4 through successive additional leftward angular iterations, if desired, may be accomplished by repeating what is set forth immediately above, until the end effector 4 returns to the neutral position and the articulation gear 40 returns to the neutral position shown in FIG. 16. After the articulation gear 40 has returned to the neutral position, end effector 4 return is complete. If the user wishes to articulate the end effector 4 further leftward, that articulation of the end effector 4 leftward may be performed as set forth above with regard to rightward articulation, but in a mirror-image manner.

Once the end effector 4 is in the desired position, the end effector 4 may be manipulated in any manner. As one example, the end effector 4 may be closed if it is open, such as by moving the anvil 32 toward the staple holder 30 to clamp tissue. The end effector 4 then may be actuated to treat tissue. As one example, where the surgical tool 2 includes one or more feeder belts 90, staples 92 may be deployed into tissue from the staple holder 6 against the anvil 4. The feeder belt or belts 90 then may be advanced, placing a fresh set of staples 92 in position for deployment within the staple holder 6. Such deployment and advancement may be accomplished as set forth in the Endocutter Documents. Afterwards, the end effector 4 may be reoriented in the manner described above, articulating the end effector 4 in a different direction, so the end effector 4 may treat tissue again. Alternately, the end effector 4 is simply withdrawn from the patient after the first tissue treatment.

The operation of the surgical tool 2 may be carried out in the course of testing at a factory or other location. If so, the user that possesses the surgical tool 2 may be a technician, machine or text fixture that exercises the surgical tool 2 in the course of testing. The term "tissue," in the context of testing the surgical tool 2 only, includes any substance or material used as a substitute for tissue in the course of testing.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. The use of terms such as "upward" and "downward" in this document refers to the orientation of parts on the page for descriptive clarity, and in no way limits the orientation of the device in use. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical apparatus, comprising:
an end effector;
a shaft extending proximally from said end effector, said shaft including an articulation region;
a handle including at least one button;
an articulation gear held by said handle;
at least one cam path defined in, and having a surface that is a portion of, said articulation gear;
at least one holder post extending into at least one said cam path and movable along and in contact with said surface of at least one said cam path wherein said at least one holder post is biased outward against a corresponding outer surface of said at least one cam path;
a spindle extending from said articulation gear; and
at least two articulation bands engaging said spindle, wherein said articulation bands extend through said shaft to said end effector;
wherein actuation of one said button engages said articulation gear and causes longitudinal motion of at least two said articulation bands, whereby said end effector articulates through a discrete angular increment relative to said shaft.

2. The surgical apparatus of claim 1, wherein at least one said cam path is defined as a depression, recess of aperture in said articulation gear.

3. The surgical apparatus of claim 1, further comprising a holder frame fixed to said handle, wherein said at least one holder post is a part of said holder frame.

4. The surgical apparatus of claim 3, wherein said holder frame includes two ends, and wherein each said end of said holder frame is one said holder post.

5. The surgical apparatus of claim 1, wherein at least one said cam path includes an outer surface, and wherein each said holder post is biased against said outer surface.

6. The surgical apparatus of claim 5, wherein at least one cam path has an outer surface, and wherein a plurality of outer notches and ramps are arranged in alternation along each said outer surface.

7. The surgical apparatus of claim 6, wherein said articulation gear is initially in a neutral position within said handle, and wherein each said holder post is biased into engagement with a corresponding said outer notch in said neutral position of said articulation gear.

8. The surgical apparatus of claim 1, wherein a holder post deflection cam is defined on at least one said button.

9. A surgical apparatus, comprising:
an end effector;
a shaft extending proximally from said end effector, said shaft including an articulation region;
a handle including at least one button;
an articulation gear held by said handle;
at least one cam path defined in, and having a surface that is a portion of, said articulation gear;
at least one holder post extending into at least one cam path and movable along and in contact with said surface of at least one said cam path;
a spindle extending from said articulation gear; and
at least two articulation bands engaging said spindle, wherein said articulation bands extend through said shaft to said end effector;
wherein actuation of one said button engages said articulation gear and causes longitudinal motion of at least two said articulation bands, whereby said end effector changes its angular position by a discrete amount relative to said shaft.

10. The surgical apparatus of claim 9, wherein at least one said cam path is defined as a depression, recess or aperture in said articulation gear.

11. The surgical apparatus of claim 9, further comprising a holder frame fixed to said handle, wherein said at least one holder post is a part of said holder frame.

12. The surgical apparatus of claim 11, wherein said holder frame includes two ends, and wherein each said end of said holder frame is one said holder post.

13. The surgical apparatus of claim 9, wherein at least one said cam path includes an outer surface, and wherein each said holder post is biased against said outer surface.

14. The surgical apparatus of claim 13, wherein at least one cam path has an outer surface, and wherein a plurality of outer notches and ramps are arranged in alteration along each said outer surface.

15. The surgical apparatus of claim 14, wherein said articulation gear is initially in a neutral position within said handle, and wherein each said holder post is biased into engagement with a corresponding said outer notch in said neutral position of said articulation gear.

* * * * *